(12) United States Patent
Jager

(10) Patent No.: US 12,251,426 B2
(45) Date of Patent: Mar. 18, 2025

(54) PHARMACOLOGICAL COMPOSITIONS FOR THE TREATMENT AND PREVENTION OF CORONAVIRUS DISEASE

(71) Applicant: Rama D. Jager, Oak Forest, IL (US)

(72) Inventor: Rama D. Jager, Oak Forest, IL (US)

(73) Assignee: Rama D. Jager, Oak Forest, IL (US)

( * ) Notice: Subject to any disclaimer, the term of this patent is extended or adjusted under 35 U.S.C. 154(b) by 66 days.

(21) Appl. No.: 17/513,395

(22) Filed: Oct. 28, 2021

(65) Prior Publication Data

US 2022/0133858 A1 May 5, 2022

Related U.S. Application Data

(60) Provisional application No. 63/107,139, filed on Oct. 29, 2020.

(51) Int. Cl.
*A61K 38/40* (2006.01)
*A61K 31/192* (2006.01)
(Continued)

(52) U.S. Cl.
CPC ............ *A61K 38/40* (2013.01); *A61K 31/192* (2013.01); *A61K 31/352* (2013.01);
(Continued)

(58) Field of Classification Search
CPC .... A61K 38/40; A61K 31/192; A61K 31/352; A61K 31/353; A61K 31/375; A61K 31/593; A61K 33/30; A61K 33/34; A61K 36/185; A61K 36/9068; A61K 2300/00
IPC ................ A61K 38/40,31/192, 31/352, 31/353, 31/375, 31/593, 33/34, 36/185, 36/9068
See application file for complete search history.

(56) References Cited

U.S. PATENT DOCUMENTS 9,907,809 B2 * 3/2018 Phillips .............. A61K 31/7028
2004/0202733 A1 10/2004 Yatcilla et al.
(Continued)

FOREIGN PATENT DOCUMENTS

WO WO-2011092835 A1 * 8/2011 ........... A61K 31/198

OTHER PUBLICATIONS

Zhang L, Liu Y. Potential interventions for novel coronavirus in China: a systematic review. J Med Virol. May 2020;92(5):479-490. doi: 10.1002/jmv.25707. Epub Mar. 3, 2020. PMID: 32052466; PMCID: PMC7166986. (Year: 2020).*

(Continued)

*Primary Examiner* — Trevor Love
*Assistant Examiner* — Janet Joseph
(74) *Attorney, Agent, or Firm* — Amin, Turocy & Watson, LLP

(57) ABSTRACT

Compositions and methods for treatment and prevention of coronavirus disease (COVID-19) and related diseases are provided. In one or more embodiments, the composition comprises two or more active ingredients selected from the group consisting of: ascorbic acid, cholecalciferol, zinc (as zinc citrate dihydrate or other forms of elemental zinc), copper (as copper gluconate or other forms of elemental copper), epigallocatechin gallate (or other flavonoids found within green tea), quercetin (as quercetin dihydrate or other forms of quercetin), hesperidin, caffeic acid, bovine lactoferrin and derivatives of the active ingredients.

9 Claims, 11 Drawing Sheets

Table 100

Table 100
(Continued)

(51) Int. Cl.

| | |
|---|---|
| *A61K 31/352* | (2006.01) |
| *A61K 31/353* | (2006.01) |
| *A61K 31/375* | (2006.01) |
| *A61K 31/593* | (2006.01) |
| *A61K 33/30* | (2006.01) |
| *A61K 33/34* | (2006.01) |
| *A61K 36/185* | (2006.01) |
| *A61K 36/9068* | (2006.01) |

(52) U.S. Cl.
CPC .......... *A61K 31/353* (2013.01); *A61K 31/375* (2013.01); *A61K 31/593* (2013.01); *A61K 33/30* (2013.01); *A61K 33/34* (2013.01); *A61K 36/185* (2013.01); *A61K 36/9068* (2013.01)

(56) References Cited

U.S. PATENT DOCUMENTS

| | | | |
|---|---|---|---|
| 2006/0241059 A1 | 10/2006 | Keller | |
| 2010/0092497 A1* | 4/2010 | Kanwar ............... | A61K 31/593 514/2.5 |
| 2011/0206786 A1* | 8/2011 | West ...................... | A61P 37/08 424/727 |
| 2012/0134952 A1 | 5/2012 | Snyder et al. | |
| 2020/0108086 A1 | 4/2020 | Phillips et al. | |
| 2020/0281972 A1 | 9/2020 | Abbott et al. | |
| 2021/0369674 A1* | 12/2021 | Wan ..................... | A61K 31/706 |

OTHER PUBLICATIONS

Amazon.com: Jarrow Formulas Green Tea 500 mg—100 veggie capsules . . . (n.d.). https://amazon.com/Jarrow-Formulas-Supports-Cardiovascular-Immune/dp/B000IZXZMC (Year: 2017).*

Dr. Cannell's advanced DTM women's formula. Purity Products. (n.d.). https://purityproducts.com/. (Year: 2012).*

NatureBell. (n.d.). https://www.amazon.com/Supplement-Vitamin-Capsules-Vitamins-Antioxidant. (Year: 202).*

Wegmüller et al.Zinc Absorption by Young Adults from Supplemental Zinc Citrate Is Comparable with That from Zinc Gluconate and Higher than from Zinc Oxide1, 2, 3, The Journal of Nutrition, vol. 144, Issue 2,2014, pp. 132-136, ISSN 0022-3166, https://doi.org/10.3945/jn.113.181487. (Year: 2014).*

Prasad A.S. et al., "Zinc: an Overview", Nutrition, vol. 11, Jan.-Feb. 1995.

Booth et al., "Metabolic Fate of Hesperidin, Eriodictyol, Homoeriodictyol, and Diosmin", JBC, vol. 230, No. 2, Feb. 1958, pp. 661-668.

"The Age-Related Eye Disease Study (AREDS): Design Implications AREDS Report No. 1", Control Clinical Trials, vol. 20, No. 6, Dec. 1999, pp. 573-600.

Gruenwald et al., "Safety and Tolerance of Ester-C Compared With Regular Ascorbic Acid", Advances In Natural Therapy, vol. 23, No. 1, Jan.-Feb. 2006, pp. 171-178.

Verlangieri et al., "Comparison of the Anti-scorbutic Activity of L-ascorbic Acid and Ester C in the Non-ascorbate Synthesizing Osteogenic Disorder Shionogi (ODS) Rat", Life Sciences, vol. 48, No. 23, 1991, pp. 2275-2281.

Straten et al., "Preventing the Common Cold With a Vitamin C Supplement: a Double-blind, Placebo-controlled Survey", Advances In Natural Therapy, vol. 19, No. 3, May-Jun. 2002, pp. 151-159.

Brody S., "High-dose Ascorbic Acid Increases Intercourse Frequency and Improves Mood: a Randomized Controlled Clinical Trial", Biological Psychiatry, vol. 52, 2002, vol. 52, pp. 371-374.

Yun et al., "Vitamin C Selectively Kills KRAS and BRAF Mutant Colorectal Cancer Cells by Targeting GAPDH", Science, vol. 350, Dec. 11, 2015, pp. 1391-1396.

Cairns R., "Drivers of the Warburg Phenotype", The Cancer Journal, vol. 21, No. 2, Mar.-Apr. 2015, pp. 56-61.

Roohi et al., "Effect of Vitamin C Supplementation on Lipid Peroxidation, Muscle Damage and Inflammation After 30-min Exercise at 75% VO2max", The Journal of Sports Medicine and Physical Fitness, vol. 48, No. 2, Jun. 2008, pp. 217-214.

Davison et al., "Influence of Acute Vitamin C and/or Carbohydrate Ingestion on Hormonal, Cytokine, and Immune Responses to Prolonged Exercise", International Journal of Sport Nutrition and Exercise Metabolism, vol. 15, No. 5, Oct. 2005, pp. 465-479.

Ristow et al., "Antioxidants Prevent Health-promoting Effects of Physical Exercise in Humans", PNAS, vol. 106, No. 21, May 26, 2009, pp. 8665-8670.

Morrison et al., "Vitamin C and E Supplementation Prevents Some of the Cellular Adaptations to Endurance-training in Humans", Free Radical Biology and Medicine, vol. 89, Dec. 2015, pp. 852-862.

Silagy et al., "Garlic as a Lipid Lowering Agent—a Meta-Analysis", Journal of the Royal College of Physicians of London, vol. 28, No. 1, Jan.-Feb. 1994, pp. 39-45.

Ashraf et al., "Garlic (Allium Sativum) Supplementation With Standard Antidiabetic Agent Provides Better Diabetic Control in Type 2 Diabetes Patients", Pakistan Journal of Pharmaceutical Sciences, vol. 24, No. 4, Oct. 2011, pp. 565-570.

Morris et al., "Effects of Garlic Consumption on Physiological Variables and Performance During Exercise in Hypoxia", Applied Physiology, Nutrition, and Metabolism, vol. 38, Mar. 20, 2013, pp. 363-367.

Josling P., "Preventing the Common Cold With a Garlic Supplement: a Double-blind, Placebo-controlled Survey", Advances in therapy, vol. 18, No. 4, Jul.-Aug. 2001, pp. 189-193.

Moyad et al., "Vitamin C With Metabolites: Additional Analysis Suggests Favorable Changes in Oxalate", Urologic Nursing, vol. 29, No. 5, Sep.-Oct. 2009, pp. 383-385.

Bae et al., "In Vitro Anti-Helicobacter Pylori Activity of Some Flavonoids and Their Metabolites", Planta Medica, vol. 65, No. 5, 1999, pp. 442-443.

Bailey et al., "Naringin is a Major and Selective Clinical Inhibitor of Organic Anion-Transporting Polypeptide 1A2 (OATP1A2) in Grapefruit Juice", Clinical Pharmacology & Therapeutics, vol. 81, No. 4, Apr. 2007, pp. 495-502.

Bates, C J., "Bioavailability of Vitamin C", European Journal of Clinical Nutrition 51(Suppl), 1997, pp. S28-S33.

Brewer et al., "Treatment of Wilson's Disease with Zinc: XI. Interaction with Other Anticopper Agents", Journal of American College of Nutrition, vol. 12, No. 1, 1993, pp. 26-30.

Centers for Disease Control (CDC), "Poisoning from Elderberry Juice—California", Morbidity Mortality Weekly Reports, Apr. 6, 1984, vol. 33, No. 13, pp. 173-174.

Chebi, "CHEBI:28411—Allicin", Jul. 15, 2015, 2 pages.

Cho et al., "Effect of Hesperidin on the Oral Pharmacokinetics of Diltiazem and Its Main Metabolite, Desacetyldiltiazem, in Rats", The Journal of Pharmacy and Pharmacology, vol. 61, Jun. 2009, pp. 825-829.

Day et al., "Dietary Flavonoid and Isoflavone Glycosides Are Hydrolysed by the Lactase Site of Lactase Phlorizin Hydrolase", FEBS Letters, vol. 468, 2000, pp. 166-170.

Dhariwal et al., "Ascorbic Acid and Dehydroascorbic Acid Measurements in Human Plasma and Serum", The American Journal of Clinical Nutrition, vol. 54, No. 4, 1991, pp. 712-716.

Fujita et al., "Comparative Evaluation of 12 Immature Citrus Fruit Extracts for the Inhibition of Cytochrome P450 Isoform Activities", Biological and Pharmaceutical Bulletin, vol. 31, No. 5, May 2008, pp. 925-930.

Hickey et al., "Dynamic Flow: A New Model for Ascorbate", Journal of Orthomolecular Medicine, vol. 20, No. 4, 2005, pp. 237-244.

HMDB, "Epigallocatechin gallate (HMDB0003153)", The Metabolomics Innovation Centre, May 22, 2006, 30 pages.

Hooper et al., "Zinc Lowers High-Density Lipoprotein-Cholesterol Levels", JAMA, vol. 244, No. 17, Oct. 24/31, 1980, pp. 1960-1961.

Hummel et al., "The Vitamin D System is Deregulated in Pancreatic Diseases", The Journal of Steroid Biochemistry and Molecular Biology, vol. 144, Part B, 2014, pp. 402-409.

Jin et al., "Effects of Gut Microflora on Pharmacokinetics of Hesperidin: a Study on Non-Antibiotic and Pseudo-Germ-Free Rats", Journal of Toxicology and Environmental Health, Part A, vol. 73, 2010, pp. 1441-1450.

(56) References Cited

OTHER PUBLICATIONS

Johnson et al., "High Dose Zinc Increases Hospital Admissions Due to Genitourinary Complications", The Journal of Urology, vol. 177, Feb. 2007, pp. 639-643.
Johnston et al., "Comparison of the Absorption and Excretion of Three Commercially Available Sources of Vitamin C", Journal of American Dieteic Association, vol. 94, No. 7, Jul. 1994, pp. 779-781.
Kim et al., "Biotransformation of Ginsenoside Rb1, Crocin, Amygdalin, Geniposide, Puerarin, Ginsenoside Re, Hesperidin, Poncirin, Glycyrrhizin, and Baicalin by Human Fecal Microflora and Its Relation to Cytotoxicity Against Tumor Cells", Journal of Microbiology and Biotechnology, vol. 18, No. 6, 2008, pp. 1109-1114.
Koshiishi et al., "Degradation of Dehydroascorbate to 2,3-Diketogulonate in Blood Circulation", Biochimica et Biophysica Acta (BBA)—General Subjects, vol. 1425, No. 1, Sep. 16, 1998, pp. 209-214.
Lawson et al., "Allicin Bioavailability and Bioequivalence fromGarlic Supplements and Garlic Foods", Nutrients, vol. 10, No. 812, Jun. 24, 2018, 49 pages.
Lewis et al., "Zinc Gluconate: Acute Ingestion", Clinical Toxicology, vol. 36, No. 1&2, 1998, pp. 99-101.
Liang et al., "Tea Extraction Methods in Relation to Control of Epimerization of Tea Catechins", Journal of the Science of Food and Agriculture, vol. 87, No. 9, Apr. 27, 2007, pp. 1748-1752.
Lomaestro et al., "Absorption Interactions with Fluoroquinolones. 1995 Update", Drug Safety, vol. 12, No. 5, 1995, pp. 314-333.
Mason et al., "High-Dose Vitamin C Supplementation Increases Skeletal Muscle Vitamin C Concentration and SVCT2 Transporter Expression but Does Not Alter Redox Status in Healthy Males", Free Radical Biology and Medicine, vol. 77, Dec. 2014, 40 pages.
Moyad et al., "Vitamin C Metabolites, Independent of Smoking Status, Significantly Enhance Leukocyte, but Not Plasma Ascorbate Concentrations", Advances in Therapy, vol. 25, No. 10, 2008, pp. 995-1009.
Naidu, K. A., "Vitamin C in Human Health and Disease is Still a Mystery? an Overview", Nutrition Journal, vol. 2, No. 7, Aug. 21, 2003, 10 pages.
Nakamoto et al., "Antimicrobial properties of hydrophobic compounds in garlic: Allicin, Vinyldithiin, Ajoene and Diallyl Polysulfides (Review)", Experimental and Therapeutic Medicine, vol. 19, 2020, pp. 1550-1553.
"Zinc", National Institutes of Health, Retrieved on May 9, 2021, 25 pages.
"Natural Medicines", Retrieved on May 9, 2022, 1 page.
Németh et al., "Deglycosylation by Small Intestinal Epithelial Cell Beta-Glucosidases is a Critical Step in the Absorption and Metabolism of Dietary Flavonoid Glycosides in Humans", European Journal of Nutrition, vol. 42, No. 1, 2003, pp. 29-42.
Nielsen et al., "Bioavailability is Improved by Enzymatic Modification of the Citrus Flavonoid Hesperidin in Humans: a Randomized, Double-Blind, Crossover Trial", The Journal of Nutrition, vol. 136, No. 2, Feb. 2006, pp. 404-408.
Ohara et al., "Oral Intake of a Combination of Glucosyl Hesperidin and Caffeine Elicits an Anti-Obesity Effect in Healthy, Moderately Obese Subjects: a Randomized Double-Blind Placebo-Controlled Trial", Nutritional Journal, vol. 15, No. 6, 2016, 11 pages.
Heinz et al., "Quercetin Supplementation and Upper Respiratory Tract Infection: a Randomized Community Clinical Trial", Pharmacological Research, vol. 62, No. 3, Sep. 2010, pp. 237-242.
Harcourt et al., "Identification of Severe Acute Respiratory Syndrome Coronavirus Replicase Products and Characterization of Papain-like Protease Activity", Journal of Virology, vol. 78, No. 24, Dec. 2004, pp. 13600-13612.
Chen et al., "SARS Coronavirus Papain-like Protease Inhibits the Type I Interferon Signaling Pathway Through Interaction with the STING-TRAF3-TBK1 Complex", Protein & Cell, vol. 5, No. 5, May 2014, 369-381.

Yuan et al., "p53 Degradation by a Coronavirus Papain-like Protease Suppresses Type I Interferon Signaling", Journal of Biological Chemistry, vol. 29, No. 5, Jan. 30, 2015, pp. 3172-3182.
Li et al., "SARS Coronavirus Papain-Like Protease Inhibits the TLR7 Signaling Pathway through Removing Lys63-Linked Polyubiquitination of TRAF3 and TRAF6", International Journal of Molecular Sciences, vol. 17, No. 5, May 2016, 10 pages.
Wang et al., "Green Tea Catechins Inhibit Pancreatic Phospholipase A(2) and Intestinal Absorption of Lipids in Ovariectomized Rats", Journal of Nutritional Biochemistry, vol. 17, No. 7, Jul. 2006, pp. 492-498.
Hu et al., "The Safety of Green Tea and Green Tea Extract Consumption in Adults-Results of a Systematic Review", Regulatory Toxicology and Pharmacology, vol. 95, Jun. 2018, pp. 412-433.
Garg et al., "Chemistry and Pharmacology of the Citrus Bioflavonoid Hesperidin", Phytotherapy Research, vol. 15, No. 8, Dec. 2001, pp. 655-669.
Endres J.R., "Letter regarding GRAS Notice No. GRN 000796", Feb. 20, 2019, 4 pages, https://www.fda.gov/media/121985/download.
Utomo et al., "Revealing the Potency of Citrus and Galangal Constituents to Halt SARS-COV-2 Infection", Mar. 12, 2020, 8 pages.
Wessels et al., "Zinc as a Gatekeeper of Immune Function", Nutrients, vol. 9, No. 12, Dec. 2017, 44 pages.
Hasse et al., "Correlation Between Zinc Status and Immune Function in the Elderly", Biogerontology, vol. 7, Nos. 5-6, Oct.-Dec. 2006, pp. 421-428.
Hsu et al., "Evaluation of Metal-conjugated Compounds as Inhibitors of 3CL Protease of SARS-CoV", Febs Letters, vol. 574, Nos. 1-3, Sep. 10, 2004, pp. 116-120.
Han et al., "Papain-like Protease 2 (PLP2) from Severe Acute Respiratory Syndrome Coronavirus (SARS-CoV): Expression, Purification, Characterization, and Inhibition", Biochemistry, vol. 44, No. 30, Aug. 2, 2005, pp. 10349-10359.
Te Velthuis et al., "Zn(2+) Inhibits Coronavirus and Arterivirus RNA Polymerase Activity in Vitro and Zinc Ionophores Block the Replication of These Viruses in Cell Culture", PLOS Pathogens, vol. 6, No. 11, Nov. 4, 2010, 11 pages.
FDA, "Frequently Asked Questions on Botanical Drug Product Development", Nov. 2, 2021, 4 pages.
Cialdella-Kam et al., "Dose-Response to 3 Months of Quercetin-containing Supplements on Metabolite and Quercetin Conjugate Profile in Adults", British Journal of Nutrition, vol. 109, 2013, pp. 1923-1933.
MAcRAE et al., "Dietary Antioxidant Supplementation Combined With Quercetin Improves Cycling Time Trial Performance", International Journal of Sport Nutrition and Exercise Metabolism, vol. 16, No. 4, Aug. 2006, pp. 405-419.
Davis et al., "The Dietary Flavonoid Quercetin Increases VO(2max) and Endurance Capacity", International Journal of Sport Nutrition and Exercise Metabolism, vol. 20, Feb. 2010, pp. 56-62.
Kaushik et al., "Comparison of Quercetin Pharmacokinetics Following Oral Supplementation in Humans", Journal of Food Science, vol. 77, No. 11, Nov. 2012, pp. 231-238.
Castellino et al., "Altilix ® Supplement Containing Chlorogenic Acid and Luteolin Improved Hepatic and Cardiometabolic Parameters in Subjects with Metabolic Syndrome: a 6 Month Randomized, Double-Blind, Placebo-Controlled Study", Nutrients, vol. 11, 2019, 17 pages.
Taliou et al., "An Open-label Pilot Study of a Formulation Containing the Anti-inflammatory Flavonoid Luteolin and Its Effects on Behavior in Children With Autism Spectrum Disorders", Clinical Therapeutics, vol. 35, No. 5, May 2013, pp. 592-602.
Arch Ophthalmol, "A Randomized, Placebo-controlled, Clinical Trial of High-dose Supplementation With Vitamins C and E, Beta Carotene, and Zinc for Age-related Macular Degeneration and Vision Loss", ARDS Report No. 8, Oct. 2001, vol. 119, No. 10, pp. 1417-1436.
Wegmuller et al., "Zinc Absorption by Young Adults From Supplemental Zinc Citrate is Comparable With That From Zinc Gluconate and Higher Than From Zinc Oxide", The Journal of Nutrition, vol. 144, Feb. 2014, pp. 132-136.

(56) References Cited

OTHER PUBLICATIONS

Prasad et al., "Duration and Severity of Symptoms and Levels of Plasma Interleukin-1 Receptor Antagonist, Soluble Tumor Necrosis Factor Receptor, and Adhesion Molecules in Patients With Common Cold Treated With Zinc Acetate", The Journal of Infectious Diseases, vol. 197, Issue 6, Mar. 15, 2008, pp. 795-802.
Turner et al., "Effect of Treatment With Zinc Gluconate or Zinc Acetate on Experimental and Natural Colds", Clinical Infectious Diseases, vol. 31, Issue 5, Nov. 15, 2000, pp. 1202-1208.
Newsome et al., "Oral zinc in Macular Degeneration", Arch Ophthalmology, vol. 106, No. 2, 1988, pp. 192-198.
Stur et al., "Oral Zinc and the Second Eye in Age-related Macular Degeneration", Investigative Ophthalmology & Visual Science, vol. 37, No. 7, Jun. 1996, pp. 1225-1235.
Picon et al., "Randomized Clinical Trial of a Phytotherapie Compound Containing Pimpinella Anisum, Foeniculum Vulgare, Sambucus Nigra, and Cassia Augustifolia for Chronic Constipation", BMC Complementary and Alternative Medicine, vol. 10, 2010, 10 pages.
Zakay-Rones et al., "Randomized Study of the Efficacy and Safety of Oral Elderberry Extract in the Treatment of Influenza a and B Virus Infections", The Journal of International Medical Research, vol. 32, 2004, pp. 132-140.
"Elderberry for Influenza", The Medical Letter on Drugs and Therapeutics, vol. 61, Feb. 25, 2019, pp. 32-33.
"The ABC Clinical Guide to Elder Berry", The American Botanical Council, European Elder Berry, Sambucus Nigra L., 2004, 12 pages.
Manson et al., "Vitamin D Supplements and Prevention of Cancer and Cardiovascular Disease", The New England Journal of Medicine, Jan. 3, 2019, vol. 380, pp. 33-44.
Bjelakovic et al., "Vitamin D Supplementation for Prevention of Mortality in Adults", The Cochrane Database of Systematic Reviews, Jan. 10, 2014, 211 pages.
Glade, M. J., "A 21st Century Evaluation of the Safety of Oral Vitamin D", Nutrition, vol. 28, No. 4, Apr. 2012, pp. 344-356.
Smit et al., "The Effect of Vitamin D and Frailty on Mortality among Non-Institutionalized Us Older Adults", European Journal of Clinical Nutrition, vol. 66, Sep. 2012, pp. 1024-1028.
Noordam et al., "Levels of 25-Hydroxyvitamin D in Familial Longevity: the Leiden Longevity Study", CMAJ, vol. 184, No. 18, Dec. 11, 2012, pp. 963-968.
Wehr et al., "Association of Vitamin D Status With Serum Androgen Levels in Men", Clinical Endrocrinology, vol. 73, No. 2, Aug. 2010, pp. 243-248.
Pilz et al., "Effect of Vitamin D Supplementation on Testosterone Levels in Men", Hormone and Metabolic Research, vol. 43, No. 3, Mar. 2011, pp. 223-235.
Terrier et al., "Restoration of Regulatory and Effector T Cell Balance and B Cell Homeostasis in Systemic Lupus Erythematosus Patients Through Vitamin D Supplementation", Arthritis Research & Therapy, vol. 14, Oct. 17, 2012, 10 pages.
Brown et al., "Effects of Dietary Supplementation With the Green Tea Polyphenol Epigallocatechin-3-gallate on Insulin Resistance and Associated Metabolic Risk Factors: Randomized Controlled Trial", The British Jounal of Nutrition, vol. 101, No. 6, Mar. 2009, pp. 886-894.
Princen et al., "No Effect of Consumption of Green and Black Tea on Plasma Lipid and Antioxidant Levels and on LDL Oxidation in Smokers", Arteriosclerosis, Thrombosis, and Vascular Biology, vol. 18, No. 5, May 1998, pp. 833-841.
Nakachi et al., "Influence of Drinking Green Tea on Breast Cancer Malignancy Among Japanese Patients", Japanese Journal of Cancer Research, vol. 89, Mar. 1998, pp. 254-261.
Hartman et al., "Tea and Coffee Consumption and Risk of Colon and Rectal Cancer in Middle-aged Finnish Men", Nutrition and Cancer, vol. 31, No. 1, 1998, pp. 41-48.
Leenen et al., "A Single Dose of Tea With or Without Milk Increases Plasma Antioxidant Activity in Humans", European Journal of Clinical Nutrition, vol. 54, 1998, pp. 87-92.

Van Het Hof et al., "Plasma and Lipoprotein Levels of Tea Catechins Following Repeated Tea Consumption", Proceedings of the Society for Experimental Biology and Medicine, vol. 220, No. 4, Apr. 1999, pp. 203-209.
Dulloo et al., "Efficacy of a Green Tea Extract Rich in Catechin Polyphenols and Caffeine in Increasing 24-h Energy Expenditure and Fat Oxidation in Humans", The American Journal of Clinical Nutrition, vol. 70, Issue 6, Dec. 1999, 1040-1045.
Geleijnse et al., "Tea Flavonoids May Protect Against Atherosclerosis: the Rotterdam Study", Archives of Internal Medicine, vol. 159, No. 18, Oct. 11, 1999, pp. 2170-2174.
Sesso et al., "Coffee and Tea Intake and the Risk of Myocardial Infarction", American Journal of Epidemiology, vol. 149, No. 2, 1999, pp. 162-167.
Ishikawa et al., "Effect of Tea Flavonoid Supplementation on the Susceptibility of Low-density Lipoprotein to Oxidative Modification", The American Journal of Clinical Nutrition, vol. 66, Aug. 1997, pp. 261-266.
Thole et al., "A Comparative Evaluation of the Anticancer Properties of European and American Elderberry Fruits", Journal of Medicinal Food, 2006, vol. 9, No. 4, pp. 498-504.
Bikle, Daniel D., "Vitamin D Metabolism, Mechanism of Action, and Clinical Applications", Chemical Biology, vol. 21, No. 3, Mar. 20, 2014, pp. 319-329.
Capiati et al., "1,25(OH)2-Vitamin D3 Induces Translocation of the Vitamin D Receptor (VDR) to the Plasma Membrane in Skeletal Muscle Cells", Journal of Cellular Biochemistry, vol. 86, No. 1, 2002, pp. 128-135.
Dawson-Hughes et al., "Meal Conditions Affect the Absorption of Supplemental Vitamin D3 but Not the Plasma 25-Hydroxyvitamin D Response to Supplementation", The Journal of Bone and Mineral Research, vol. 28, Issue 8, Aug. 2013, pp. 1778-1783.
Krishnan et al., "Equivalent Anticancer Activities of Dietary Vitamin D and Calcitriol in an Animal Model of Breast Cancer: Importance of Mammary CYP27B1 for Treatment and Prevention", The Journal of Steroid Biochemistry and Molecular Biology, vol. 136, 2013, pp. 289-295.
Fernandes et al., "Physical Exercise as an Epigenetic Modulator of Brain Plasticity and Cognition", Neuroscience & Biobehavioral Reviews, vol. 80, Sep. 2017, pp. 443-456.
Gorkom et al., "Influence of Vitamin C on Lymphocytes: an Overview", Antioxidants, vol. 7, No. 41, 2018, 14 pages.
Hajishengallis G., "Too old to fight? Aging and its toll on innate immunity", Molecular Oral Microbiology, 2010, vol. 25, pp. 25-37.
Monsen, E. R., "Dietary Reference Intakes for the Antioxidant Nutrients: Vitamin C, Vitamin E, Selenium, and Carotenoids," Journal of the American Dietetic Association, vol. 100, 2000, pp. 637-640.
Watson R., "Handbook of Nutrition in the Aged" CRC Press Inc.; Boca Raton, FL, USA, 1985, pp. 157-185.
Simon et al., "Relation of Serum Ascorbic Acid to Mortality Among Us Adults", Journal of the American College of Nutrition, vol. 20, No. 3, Jun. 2001, pp. 255-263.
Fletcher et al., "Antioxidant Vitamins and Mortality in Older Persons: Findings From the Nutrition Add-on Study to the Medical Research Council Trial of Assessment and Management of Older People in the Community", The American Journal of Clinical Nutrition, vol. 78, No. 5, Nov. 2003, pp. 999-1010.
Thurman et al., "Vitamin Supplementation Therapy in the Elderly", Drugs Aging, vol. 11, 1997, pp. 433-449.
Hanck A., "Vitamin C in the Elderly", International Journal for Vitamin and Nutrition Research. Supplement, vol. 24, 1983, pp. 257-269.
Schorah C.J., "The Level of Vitamin C Reserves Required in Man: Towards a Solution to the Controversy", The Proceedings of the Nutrition Society, vol. 40, 1981, pp. 147-154.
Hunt et al., "The Clinical and Biochemical Effects of Vitamin C Supplementation in Short-stay Hospitalized Geriatric Patients", International Journal for Vitamin and Nutrition Research, vol. 54, 1984, pp. 65-74.
Mayland et al., "Vitamin C deficiency in cancer patients" Palliative Medicine, vol. 19, 2005, pp. 17-20.

(56) References Cited

OTHER PUBLICATIONS

Danai et al., "The Epidemiology of Sepsis in Patients With Malignancy" Chest., vol. 129, 2006, pp. 1432-1440.
Gan et al., "Vitamin C Deficiency in a University Teaching Hospital", Journal of the American College of Nutrition, Vo. 27, 2008, pp. 428-433.
Dahl et al., "The Effect of Ascorbic Acid on Production of Human Interferon and the Antiviral Activity in Vitro", Acta Pathologica Microbiologica Scandinavica Section B Microbiology, vol. 84, 1976, pp. 280-284.
Karpińska et al., "The Influence of Ultraviolet Irradiation, L-Ascorbic Acid and Calcium Chloride on the Induction of Interferon in Human Embryo Fibroblasts", Archivum Immunologiae et Therapiae Experimentalis, vol. 30, 1982, pp. 33-37.
Siegel B.V., Enhancement of Interferon Production by Poly(Ri)-Poly(Rc) in Mouse Cell Cultures by Ascorbic Acid, Nature, vol. 254, Apr. 10, 1975, pp. 531-532.
Porter et al., "A Review of the Antiviral Properties of Black Elder (Sambucus Nigra L.) Products", Phytotherapy Research, vol. 31, No. 4, Apr. 2017, pp. 533-554.
Serkedjieva et al., "Antiviral Activity of the Infusion (SHS-174) From Flowers of Sambucus Nigra L., Aerial Parts of Hypericum Perforatum L., and Roots of Saponaria Officinalis L. Against Influenza and Herpes Simplex Viruses", Phytotherapy Research, vol. 4, 1990, pp. 97-100.
Zakay-Rones et al., "Inhibition of Several Strains of Influenza Virus in Vitro and Reduction of Symptoms by an Elderberry Extract (Sambucus Nigra L.) During an Outbreak of Influenza B Panama", Journal of Alternative and Complementary Medicine, vol. 1, No. 4, 1995, pp. 361-369.
Amoros et al., "Synergistic Effect of Flavones and Flavonols Against Herpes Simplex Virus Type 1 in Cell Culture Comparison with the Antiviral Activity of Propolis", Journal of Natural Products, vol. 55, No. 12, 1992, pp. 1732-1740.
Mahmood et al., Inhibition of HIV Infection by Flavanoids, Antiviral Research, vol. 22, 1993, pp. 189-199.
Utsunomiya et al., "Inhibition by Caffeic Acid of the Influenza a Virus Multiplication in Vitro", International Journal of Molecular Medicine, vol. 34, No. 4, Jul. 2014, pp. 1020-1024.
Semwal et al., "Myricetin: a Dietary Molecule With Diverse Biological Activities", Nutrients, vol. 8, No. 9, 2016, 31 pages.
"Quercetin", Molecule of the Week Archive, American Chemical Society, Dec. 9, 2013.
"Quercetin (Code C792)", NCIthesaurus, Mar. 28, 2022, p. 1.
"Luteolin (Code C68467)", NCIthesaurus, Mar. 28, 2022, p. 1.
Zhao et al., "Inhibition of Pattern Recognition Receptor-mediated Inflammation by Bioactive Phytochemicals: a Review of Recent Research", Nutrition Reviews, vol. 69, No. 6, Jun. 2011, 19 pages.
Guëguen et al., "Shellfish and Residual Chemical Contaminants: Hazards, Monitoring, and Health Risk Assessment Along French Coasts", Reviews of Environmental Contamination and Toxicology, vol. 213, 2011, pp. 55-111.
Abreu et al., "Superoxide Dismutases-a Review of the Metal-associated Mechanistic Variations", Biochimica et Biophysica Acta, vol. 1804, No. 2, Feb. 2010, pp. 263-274.
"A Dose of Vitamin D History", Nature Structural Biology, vol. 9, No. 2, Feb. 2002, p. 1.
Chen et al., "EGCG, Green Tea Polyphenols and Their Synthetic Analogs and Prodrugs for Human Cancer Prevention and Treatment", Advances in Clinical Chemistry, vol. 53, 2011, pp. 155-177.
"Epigallocatechin Gallate (Code C1088)", NCIthesaurus, Mar. 28, 2022, p. 1.
"Albert Szent-Györgyi's Discovery of Vitamin C", 2002, 6 pages.
"Ascorbic Acid (Code C285))", NCIthesaurus, Mar. 28, 2022, 2 pages.
Rahman M.S., "Allicin and Other Functional Active Components in Garlic: Health Benefits and Bioavailability", International Journal of Food Properties, vol. 10, 2007, pp. 245-268.
Ji et al., "Green Tea Consumption and the Risk of Pancreatic and Colorectal Cancers", International Journal of Cancer, vol. 70, 1997, pp. 255-288.
Viswanatha et al., "Hesperidin Ameliorates Immobilization-stress-induced Behavioral and Biochemical Alterations and Mitochondrial Dysfunction in Mice by Modulating Nitrergic Pathway", ISRN Pharmacology, vol. 2012, 2012, 8 pages.
Selvaraj et al., "Hesperidin, a Flavanone Glycoside, on Lipid Peroxidation and Antioxidant Status in Experimental Myocardial Ischemic Rats", Redox Report, vol. 15, No. 5, 2010, pp. 217-223.
International Search Report and Written Opinion received for PCT Application Serial No. PCT/US2021/57113 dated Jan. 26, 2022, 14 pages.
McCutcheon et al., "Scientific and Clinical Monograph for POM Wonderful® Pomegranate Juice", American Botanical Council, 2008, pp. 1-19.
CDC, "Interim Clinical Guidance for Management of Patients with Confirmed Coronavirus Disease (COVID-19)", Centers for Disease Control And Prevention, 2021, 14 pages.
IDSA, "IDSA Guidelines on the Treatment and Management of Patients with COVID-19", Infectious Diseases Society of America, Nov. 4, 2020, 3 pages.
Junod S.W., "FDA and Clinical Drug Trials: a Short History", U.S. Food and Drug Administration, 2008, 21 pages.
CDC, "How COVID-19 Spreads", COVID-19, Centers for Disease Control And Prevention, Jul. 14, 2021, 3 pages.
Paraskeviset et al., "Full-genome Evolutionary Analysis of the Novel Corona Virus (2019-ncov) Rejects the Hypothesis of Emergence as a Result of a Recent Recombination Event", Infection, Genetics and Evolution, vol. 79, 2020, 5 pages.
Masters P. S., "The Molecular Biology of Coronaviruses", Advances in Virus Research, vol. 66, 2006, pp. 193-292.
Zhou et al., "A Pneumonia Outbreak Associated With a New Coronavirus of Probable Bat Origin", Nature, vol. 579, Mar. 12, 2020, pp. 270-273.
Hoffman et al., "SARS-CoV-2 Cell Entry Depends on ACE2 and TMPRSS2 and is Blocked by a Clinically Proven Protease Inhibitor", Cell, vol. 181, Apr. 16, 2020, pp. 271-280.
Xu et al., "Evolution of the Novel Coronavirus From the Ongoing Wuhan Outbreak and Modeling of Its Spike Protein for Risk of Human Transmission", Science China Life Sciences, vol. 63, No. 3, Mar. 2020, pp. 457-460.
Letko et al., "Functional Assessment of Cell Entry and Receptor Usage for Lineage B B-coronaviruses, Including 2019-ncov", bioRxiv, The Preprint for biology, 2020, 26 pages.
Gao et al., "Structure of the RNA-dependent RNA Polymerase from Covid-19 Virus", Science, vol. 368, No. 6492, May 15, 2020, pp. 779-782.
Hilgenfeld et al., "From SARS to MERS: Crystallographic Studies Oncoronaviral Proteases Enable Antiviral Drug Design", The FEBS Journal, vol. 281, 2014, pp. 4085-4096.
Yang et al., "The Crystal Structures of Severe Acute Respiratory Syndrome Virus Main Protease and Its Complex With an Inhibitor", PNAS, vol. 100, No. 23, Nov. 11, 2003, pp. 13190-13195.
"2DUC", Protein Data Bank, 2020, 7 pages.
"6LU7", Protein Data Bank, 2020, 5 pages.
"Using the Tolerable Upper Intake Level for Nutrient Assessment of Groups", DRI Dietary Reference Intakes: Applications in Dietary Assessment, 2000.
Liu et al., "Vitamin D Deficiency and Insufficiency Among US Adults: Prevalence, Predictors and Clinical Implications", The British Journal of Nutrition, vol. 119. No. 8, Apr. 2018, pp. 928-936.
Schleicher et al., "Serum Vitamin C and the Prevalence of Vitamin C Deficiency in the United States: 2003-2004 National Health and Nutrition Examination Survey (NHANES)", The American Journal of Clinical Nutrition, vol. 90, Issue. 5, Nov. 2009, pp. 1252-1263.
Dabbagh-Bazarbachi et al., "Zinc Ionophore Activity of Quercetin and Epigallocatechin-gallate: From Hepa 1-6 Cells to a Liposome Model", Journal of Agricultural and Food Chemistry, vol. 62, 2014, pp. 8085-8093.
Nozza et al., "Antiretroviral Therapy in Geriatric HIV Patients: the Geppo Cohort Study", Journal of Antimicrobial Chemotherapy, vol. 72, No. 10, Oct. 2017, pp. 2879-2886.

(56) References Cited

OTHER PUBLICATIONS

Stuehler et al., "Combination Therapy for Multidrug-Resistant Cytomegalovirus Disease", Transplant Infectious Disease, vol. 17, 2015, pp. 751-755.

Seaworth et al., "Therapy of Multidrug-Resistant and Extensively Drug-Resistant Tuberculosis", Microbiology Spectrum, vol. 5, No. 2, Mar. 2017, 28 pages.

Irwin et al., "Antiviral Drug Resistance as an Adaptive Process", Virus Evolution, vol. 2, Jan. 2016, 10 pages.

Pachetti et al., "Emerging SARS-CoV-2 Mutation Hot Spots Include a Novel RNA-dependent-RNA Polymerase Variant", Journal of Translational Medicine, vol. 18, 2020, 9 pages.

Guerrero et al., "Inhibition of Angiotensin-Converting Enzyme Activity by Flavonoids: Structure-Activity Relationship Studies", PLOS ONE, vol. 7, No. 11, Nov. 2012, 11 pages.

Thakkar, Vatsal G., "Vitamin D and Coronavirus Disparities", WSJ Opinion, Apr. 16, 2020, 3 pages.

Daneshkhah et al., "The Role of Vitamin D in Suppressing Cytokine Storm in COVID-19 Patients and Associated Mortality", Apr. 10, 2020, 20 pages.

Carr et al., "Vitamin C and Immune Function", Nutrients, vol. 9, Nov. 3, 2017, 25 pages.

Fisher et al., "Mechanisms of Attenuation of Abdominal Sepsis Induced Acute Lung Injury by Ascorbic Acid", The American Journal of Physiology-Lung Cellular and Molecular Physiology, vol. 303, Apr. 20, 2012, 13 pages.

Tiralongo et al., "Elderberry Supplementation Reduces Cold Duration and Symptoms in Air-Travellers: a Randomized, Double-Blind Placebo-Controlled Clinical Trial", Nutrients, vol. 8, Mar. 24, 2016, 15 pages.

Weng et al., "Antiviral Activity of Sambucus Formosananakai Ethanol Extract and Related Phenolic Acid Constituents Against Human Coronavirus NL63", Virus Research, vol. 273, 2019, 8 pages.

Smith et al., "Repurposing Therapeutics for COVID-19: Supercomputer-Based Docking to the SARS-CoV-2 Viral Spike Protein and Viral Spike Protein-Human ACE2 Interface", 2020, 28 pages.

McAnlis et al., "Absorption and Antioxidant Effects of Quercetin from Onions, in Man", Nature, European Journal of Clinical Nutrition, vol. 53, 1999, pp. 92-96.

Nguyen et al., "Flavonoid-mediated Inhibition of SARS Coronavirus 3C-like Protease Expressed in Pichia Pastoris", Biotechnol Letter, vol. 34, 2012, pp. 831-838.

Kasikci et al., "Bioavailability of Quercetin", Current Research in Nutrition and Food Science, vol. 4, 2016, pp. 146-151.

International Preliminary Report on Patentability received for PCT Application Serial No. PCT/US2021/57113 dated May 11, 2023, 6 pages.

Okamura, M., "Uptake of L-Ascorbic Acid and L-Dehydroascorbic Acid by Human Erythrocytes and HeLa Cells", Journal Nutritional Science and Vitaminology (Tokyo), vol. 25, No. 4, 1979, pp. 269-279.

Padayatty et al., "Vitamin C Pharmacokinetics: Implications for Oral and Intravenous Use", Annals of Internal Medicine, vol. 140, No. 7, Apr. 6, 2004, pp. 533-537.

Panda et al., "Vitamin C Prevents Cigarette Smoke-Induced Oxidative Damage in Vivo", Free Radical Biology and Medicine, vol. 29, No. 2, 2000, pp. 115-124.

Pentillä et al., "Effect of Zinc Sulphate on the Absorption of Tetracycline and Doxycycline in Man", European Journal of Clinical Pharmacology, vol. 9, 1975, pp. 131-134.

Rastogi et al., "Evaluation of Inhibitory Effects of Caffeic Acid and Quercetin on Human Liver Cytochrome P450 Activities", Phytotherapy Research, vol. 28, 2014, pp. 1873-1878.

Sempos et al., "25-Hydroxyvitamin D Assay Standardisation and Vitamin D Guidelines Paralysis", Public Health Nutrition, vol. 23, No. 7, 2020, pp. 1153-1164.

Sempos et al., "Vitamin D Assays and the Definition of Hypovitaminosis D: Results from the First International Conference on Controversies in Vitamin D", British Journal of Clinical Pharmacology, vol. 84, 2018, pp. 2194-2207.

Sergent et al., "CYP1A1 and CYP3A4 Modulation by Dietary Flavonoids in Human Intestinal Caco-2 Cells", Toxicology Letters, vol. 191, No. 2-3, 2009, pp. 216-222.

Sesink et al., "Intestinal Uptake of Quercetin-3-Glucoside in Rats Involves Hydrolysis by Lactase Phlorizin Hydrolase", The Journal of Nutrition, vol. 133, No. 3, 2003, pp. 773-776.

Shoskes et al., "Quercetin in Men with Category III Chronic Prostatitis: a Preliminary Prospective, Double-Blind, Placebo-Controlled Trial", Urology, vol. 54, No. 6, Dec. 1, 1999, pp. 960-963.

Singh et al., "Dietary Quercetin Exacerbates the Development of Estrogen-Induced Breast Tumors in Female ACI Rats", Toxicology and Applied Pharmacology, vol. 247, 2010, pp. 83-90.

Vieth R., "Vitamin D Supplementation, 25-Hydroxyvitamin D Concentrations, and Safety", The American Journal of Clinical Nutrition, vol. 69, 1999, pp. 842-856.

Wang et al., "Human Vitamin C (L-Ascorbic Acid) Transporter SVCT1", Biochemical Biophysical Research Communication, vol. 267, No. 2, Jan. 19, 2000, pp. 488-494.

Wang et al., "Hydrolysis of Flavanone Glycosides and Degradation of the Corresponding Aglycones from Dried Immature Citrus Fruit by Human Fecal Flora in Vitro", Planta Med, vol. 74, Oct. 30, 2008, pp. 1751-1755.

Wester P. O., "Urinary Zinc Excretion During Treatment with Different Diuretics", Acta Medica Scandinavica, vol. 208, 1980, pp. 209-212.

Institute of Medicine, Food and Nutrition Board", Dietary Reference Intakes for Calcium and Vitamin D", Washington, DC: National Academy Press, 2010.

Jin J., "Vitamin D and Calcium Supplements for Preventing Fractures", JAMA, , vol. 319, No. 15, Apr. 17, 2018, p. 1630.

Hansen et al., "Medicare Cost of Osteoporotic Fractures", Milliman Research Report, Aug. 2019, 48 pages.

Chung et al., "Vitamin D and Calcium: a Systematic Review of Health Outcomes", Evidence Report/Technology Assessment No. 183, Aug. 2009, 420 pages.

US Preventive Services Task Force, "Vitamin D, Calcium, or Combined Supplementation for the Primary Prevention of Fractures in Community-Dwelling Adults: US Preventive Services Task Force Recommendation Statement", JAMA, vol. 319, No. 15, 2018, pp. 1592-1599.

Kahwati et al., "Vitamin D, Calcium, or Combined Supplementation for the Primary Prevention of Fractures in Community-Dwelling Adults: Evidence Report and Systematic Review for the US Preventive Services Task Force", JAMA, vol. 319, No. 15, 2018, pp. 1600-1612.

Chow et al., "Effects of Dosing Condition on the Oral Bioavailability of Green Tea Catechins after Single-Dose Administration of Polyphenon E in Healthy Individuals", Clinical Cancer Research, vol. 11, No. 12, Jun. 15, 2005, pp. 4627-4633.

Ullmann et al., "A Single Ascending Dose Study of Epigallocatechin Gallate in Healthy Volunteers", The Journal of International Medical Research, vol. 31, 2003, pp. 88-101.

Chow et al., "Pharmacokinetics and Safety of Green Tea Polyphenols After Multiple-Dose Administration of Epigallocatechin Gallate and Polyphenon E in Healthy Individuals", Clinical Cancer Research, vol. 9, Aug. 15, 2003, pp. 3312-3319.

Pisters et al., "Phase I Trial of Oral Green Tea Extract in Adult Patients With Solid Tumors", Journal of Clinical Oncology, vol. 19, No. 6, Mar. 15, 2001, pp. 1830-1838.

"Body Surface Area for Adjustment of Drug Dose", Drug and Therapeutics Bulletin, vol. 48, No. 3, Mar. 2010, pp. 33-36.

Institute of Medicine, Food and Nutrition Board", Dietary Reference Intakes for Vitamin C, Vitamin E, Selenium, and Carotenoids", Washington, DC: National Academy Press, 2000.

Jacob et al., "Vitamin C Function and Status in Chronic Disease", Nutrition in Clinical Care : an Official Publication of Tufts University, Mar.-Apr. 2002, vol. 5, No. 2, pp. 66-74.

(56) References Cited

OTHER PUBLICATIONS

Carr et al., "Does Vitamin C Act as a Pro-Oxidant Under Physiological Conditions?", The FASEB Journal, vol. 13, Jun. 1999, pp. 1007-1024.
Lawenda et al., "Should Supplemental Antioxidant Administration Be Avoided During Chemotherapy and Radiation Therapy?", JNCI: Journal of the National Cancer Institute, vol. 100, Issue. 11, Jun. 4, 2008, pp. 773-783.
Ladas et al., "Antioxidants and Cancer Therapy: a Systematic Review", Journal of Clinical Oncology, Feb. 1, 2004, vol. 22, No. 3, pp. 517-528.
Ye et al., "Antioxidant Vitamins Intake and the Risk of Coronary Heart Disease: Meta-analysis of Cohort Studies", European Journal of Cardiovascular Prevention and Rehabilitation, Feb. 2008, vol. 15, No. 1, pp. 26-34.
Block et al., "Impact of Antioxidant Supplementation on Chemotherapeutic Efficacy: a Systematic Review of the Evidence From Randomized Controlled Trials", Cancer Treatment Reviews, vol. 33, No. 5, Aug. 1, 2007, pp. 407-418.
Heaney et al., "Vitamin C Antagonizes the Cytotoxic Effects of Antineoplastic Drugs", Cancer Research, vol. 68, No. 19, Oct. 1, 2008, pp. 8031-8038.
Willcox et al., "Antioxidants in Cardiovascular Health and Disease: Key Lessons from Epidemiologic Studies", The American Journal of Cardiology, vol. 101, No. 10, May 22, 2008, pp. 85-86, doi: 10.1016/j.amjcard.2008.02.012.
Prasad K.N., "Rationale for Using High-Dose Multiple Dietary Antioxidants as an Adjunct to Radiation Therapy and Chemotherapy", The Journal of Nutrition, vol. 134, No. 11, Nov. 2004, pp. 3182S-3183S.
Brown et al., "Simvastatin and Niacin, Antioxidant Vitamins, or the Combination for the Prevention of Coronary Disease", The New England Journal of Medicine, vol. 345, No. 22, Nov. 29, 2001, 1583-1592.
Cheung et al., "Antioxidant Supplements Block the Response of HDL to Simvastatin-Niacin Therapy in Patients With Coronary Artery Disease and Low HDL", Arteriosclerosis, Thrombosis, and Vascular Biology, vol. 21, No. 8, Aug. 2001, pp. 1320-1326.
U.S. FDA, "Current Good Manufacturing Practice for Phase 1 Investigational Drugs", Guidance for Industry, Jul. 2008, 20 pages.
Tahir ul Qamar et al., "Structural basis of SARS-CoV-2 3CLpro and anti-COVID-19 drug discovery from medicinal plants", Journal of Pharmaceutical Analysis, vol. 10, Issue 4, Aug. 2020, pp. 313-319.
Yi et al., "Small Molecules Blocking the Entry of Severe Acute Respiratory Syndrome Coronavirus into Host Cells", Journal of Virology, Oct. 2004, pp. 11334-11339.
Yu et al., "Identification of myricetin and scutellarein as novel chemical inhibitors of the SARS coronavirus helicase, nsP13", Bioorganic & Medicinal Chemistry Letters, 22 (2012), pp. 4049-4054.
Kono et al., "Green Tea Consumption and Serum Lipid Profiles: a Cross-sectional Study in Northern Kyushu, Japan", Preventive Medicine, vol. 21, No. 4, Jul. 1992, pp. 526-531.
Kono et al., "Relation of Green Tea Consumption to Serum Lipids and Lipoproteins in Japanese Men", Journal of Epidemiology, vol. 6, No. 3, Sep. 1996, pp. 128-133.
Imai et al., "Cancer-Preventive Effects of Drinking Green Tea among a Japanese Population", Preventive Medicine, vol. 26, Issue 6, Nov. 1997, pp. 769-775.
Wu et al., "Green Tea and Risk of Breast Cancer in Asian Americans", International Journal of Cancer, vol. 106, 2003, pp. 574-579.
Ohno et al., "Tea Consumption and Lung Cancer Risk: a Case-control Study in Okinawa, Japan", Japanese Journal of Cancer Research, vol. 86, No. 11, Nov. 1995, pp. 1027-1034.
Gao et al., "Reduced Risk of Esophageal Cancer Associated With Green Tea Consumption", Journal of the National Cancer Institute, vol. 86, No. 11, Jun. 1994, pp. 855-858.
Hegarty et al., "Tea Drinking and Bone Mineral Density in Older Women", The American Journal of Clinical Nutrition, vol. 71, No. 4, Apr. 2000, pp. 1003-1007.
Goto et al., " The Effects of Tea Catechins on Fecal Conditions of Elderly Residents in a Long-Term Care Facility", Journal of Nutritional Science and Vitaminology, vol. 45, No. 1, Jan. 1999, pp. 135-141.
The ABC Clinical Guide to Herbs, "Tea, Black/Green", Clinical Overview, 2003, pp. 335-349.
Kometani et al., "Effects of Alpha-Glucosylhesperidin, a Bioactive Food Material, on Collagen-induced Arthritis in Mice and Rheumatoid Arthritis in Humans", Immunopharmacology and Immunotoxicology, vol. 30, 2008.
Van Het Hof et al., "Consumption of Green or Black Tea Does Not Increase Resistance of Low-density Lipoprotein to Oxidation in Humans", American Journal of Clinical Nutrition, vol. 66, 1997, pp. 1125-1132.
Graefe et al., "Pharmacokinetics and Bioavailability of the Flavonol Quercetin in Humans", International Journal of Clinical Pharmacology and Therapeutics, vol. 37, No. 5, May 1999, pp. 219-233.
Aksari et al., "The Effect of Quercetin Supplementation on Selected Markers of Inflammation and Oxidative Stress", Journal of Research in Medical Sciences, vol. 17, No. 7, Jul. 2012, pp. 637-641.
Chen et al., "Cardioprotective Effects of Quercetin in Cardiomyocyte under Ischemia/Reperfusion Injury", Evidence-Based Complementary and Alternative Medicine, vol. 2013, Article ID 364519, 16 pages.
Sharmila et al., "Chemopreventive Effect of Quercetin, a Natural Dietary Flavonoid on Prostate Cancer in In-Vivo Model", Clinical Nutrition, vol. 33, No. 4, Aug. 2014, pp. 718-726.
Akan et al., "Antioxidants May Protect Cancer Cells from Apoptosis Signals and Enhance Cell Viability", Asian Pacific Journal of Cancer Prevention, vol. 14, No. 8, 2013, pp. 4611-4614.
Wang et al., "Quercetin Potentiates Doxorubicin Mediated Antitumor Effects Against Liver Cancer Through p53/BCI-XI", PLoS One, Dec. 2012, vol. 7, No. 12, 12 pages.
Rinwa et al., "Quercetin Suppress Microglial Neuroinflammatory Response and Induce Antidepressent-like Effect in Olfactory Bulbectomized Rats", Neuroscience, vol. 255, 2013, pp. 86-98.
Meng et al., "Quercetin Reduces Serum Homocysteine Level in Rats Fed a Methionine-Enriched Diet", Nutrition, vol. 29, No. 4, Apr. 2013, pp. 661-666.
Hollman et al., "Absorption of Dietary Quercetin Glycosides and Quercetin in Healthy Ileostomy Volunteers", The American Journal of Clinical Nutrition, vol. 62, Issue 6, Dec. 1995, pp. 1276-1282.
Kaushik et al., "Comparison of Quercetin Pharmacokinetics Following Oral Supplementation in Humans", Food Science, vol. 77, Issue 11, Nov. 2012, pp. H231-H238.
Graefe et al., "Pharmacokinetics and Bioavailability of Quercetin Glycosides in Humans", The Journal of Clinical Pharmacology, vol. 41, Issue 5, May 2001, pp. 492-499.
"Luteolin (HMDB0005800)", Jan. 22, 2017, 21 pages.
Lupu et al., "Pharmacological Inhibitors of Fatty Acid Synthase (FASN)—Catalyzed Endogenous Fatty Acid Biogenesis: a New Family of Anti-Cancer Agents?", Current Pharmaceutical Biotechnology, Dec. 2006, vol. 7, No. 6, pp. 483-493.
Goedert et al., "Fecal Metabolomics: Assay Performance and Association with Colorectal Cancer", Carcinogenesis, vol. 35, No. 9, Sep. 2014, pp. 2089-2096.
Kandaswami et al. "The Antitumor Activities of Flavonoids", In Vivo, vol. 19, No. 5, Sep.-Oct. 2005, pp. 895-909.
Prasad, Ananda S., "Discovery of Human Zinc Deficiency: Its Impact on Human Health and Disease", Advances in Nutrition, vol. 4, No. 2, 2013, pp. 176-190.
"Dietary Reference Intakes for Vitamin A, Vitamin K, Arsenic, Boron, Chromium, Copper, Iodine, Iron, Manganese, Molybdenum, Nickel, Silicon, Vanadium, and Zinc", Institute of Medicine (US) Panel on Micronutrients, Washington (DC): National Academies Press (US), 2001, 797 pages.
Maret, W., "Zinc Biochemistry: From a Single Zinc Enzyme to a Key Element of Life", Advances in Nutrition, vol. 4, No. 1, Jan. 2013, pp. 82-91.
Coelho et al., "Zinc as a Possible Treatment for Tinnitus", Progress in Brain Research, vol. 166, 2007, pp. 279-285.

(56) References Cited

OTHER PUBLICATIONS

Haylard, M. Y., "Taste and Smell Alterations in Cancer Patients-Real Problems with Few Solutions", The Journal of Supportive Oncology, vol. 7, No. 2, Mar.-Apr. 2009, pp. 68-69.
Yamaguchi, M., "Role of Nutritional Zinc in the Prevention of Osteoporosis", Molecular and Cellular Biochemistry, vol. 338, No. 1-2, May 2010, pp. 241-254.
Korant et al., "Inhibition by Zinc of Rhinovirus Protein Cleavage: Interaction of Zinc with Capsid Polypeptides", Journal of Virology, vol. 18, No. 1, Apr. 1976, pp. 298-306.
Tuerk et al., "Zinc Deficiency", Current Opinion in Gastroenterology, vol. 25, No. 2, Mar. 2009, pp. 136-143.
Omu et al., "Indications of the Mechanisms Involved in Improved Sperm Parameters by Zinc Therapy", Medical Principles and Practice, vol. 17, No. 2, 2008, pp. 108-116.
Alam et al., "Cellular Mechanisms of Zinc Dysregulation: a Perspective on Zinc Homeostasis as an Etiological Factor in the Development and Progression of Breast Cancer", Nutrients, vol. 4, No. 8, Aug. 2012, pp. 875-903.
Kelleher et al., "Mammary Gland Zinc Metabolism: Regulation and Dysregulation", Genes & Nutrition, vol. 4, No. 2, Jun. 2009, pp. 83-94.
Kolenko et al., "Zinc and Zinc Transporters in Prostate Carcinogenesis", Nature Reviews Urology, vol. 10, No. 4, Apr. 2013, 219-226.
Liang et al., "Inhibitory Effect of Zinc on Human Prostatic Carcinoma Cell Growth", Prostate, vol. 40, No. 3, Aug. 1999, pp. 200-207.
Han et al., "Influence of Zinc Deficiency on Akt-Mdm2-P53 and Akt-P21 Signaling Axes in Normal and Malignant Human Prostate Cells", American Journal of Physiology-Cell Physiology, vol. 297, No. 5, Nov. 2009, pp. C1188-C1199.
Taccioli et al., "Zinc Replenishment Reverses Overexpression of the Proinflammatory Mediator S100A8 and Esophageal Preneoplasia in the Rat", Gastroenterology, vol. 136, No. 3, Mar. 2009, pp. 953-966.
Taccioli et al., "Dietary Zinc Deficiency Fuels Esophageal Cancer Development by Inducing a Distinct Inflammatory Signature", Oncogene, vol. 31, No. 42, Oct. 18, 2012, pp. 4550-4558.
Roschek et al., "Elderberry Flavonoids Bind to and Prevent H1N1 Infection in Vitro", Phytochemistry, vol. 70, No. 10, Jul. 2009, pp. 1255-1261.
Fink et al., "HIV Type-1 Entry Inhibitors with a New Mode of Action", Antiviral Chemistry & Chemotherapy, vol. 19, 2009, pp. 243-255.
Krawitz et al., "Inhibitory Activity of a Standardized Elderberry Liquid Extract Against Clinically-Relevant Human Respiratory Bacterial Pathogens and Influenza a and B Viruses", BMC Complementary and Alternative Medicine, vol. 11, No. 7, 2011, 6 pages.
Barak et al., "The Effect of Herbal Remedies on the Production of Human Inflammatory and Anti-Inflammatory Cytokines", The Israel Medical Association Journal, vol. 4, Suppl. 11, Nov. 2002, pp. 919-922.
Farrell et al., "Black Elderberry Extract Attenuates Inflammation and Metabolic Dysfunction in Diet-Induced Obese Mice", British Journal of Nutrition, vol. 114, 2015, pp. 1123-1131.
Christensen et al., "Identification of Bioactive Compounds from Flowers of Black Elder (Sambucus Nigra L.) that Activate the Human Peroxisome Proliferator-Activated Receptor (PPAR) Gamma", Phytotherapy Research, vol. 24, Issue S2, Jun. 2010, pp. S129-S132.
"Cranberry Vaccinium macrocarpon Aiton" Clinical Overview, The ABC Clinical Guide to Herbs, 2003, pp. 73-83.
"Quercetin", Compound Summary, PubChem, C15H1007, online available <https://pubchem.ncbi.nlm.nih.gov/compound/Quercetin>, retrieved on Apr. 19, 2024, 96 pages.
"Luteolin", Compound Summary, PubChem, C15H1006, online available <https://pubchem.ncbi.nlm.nih.gov/compound/Luteolin>, retrieved on Apr. 19, 2024, 60 pages.
"Zinc citrate", Compound Summary, PubChem, C12H10O14Zn3, online available <https://pubchem.ncbi.nlm.nih.gov/compound/Zinc-Citrate>, retrieved on Apr. 19, 2024, 27 pages.
"Cholecalciferol", Compound Summary, PubChem, C27H440, online available <https://pubchem.ncbi.nlm.nih.gov/compound/Cholecalciferol>, retrieved on Apr. 19, 2024, 101 pages.
"Epigallocatechin gallate", Compound Summary, PubChem, C22H18011, online available <https://pubchem.ncbi.nlm.nih.gov/compound/Epigallocatechin-Gallate>, retrieved on Apr. 19, 2024, 51 pages.
"Ascorbic acid", Compound Summary, PubChem, HC6H706, online available <https://pubchem.ncbi.nlm.nih.gov/compound/Ascorbic-Acid>, retrieved on Apr. 19, 2024, 140 pages.
"Allicin", Compound Summary, PubChem, C6H10OS2, online available <https://pubchem.ncbi.nlm.nih.gov/compound/Allicin>, retrieved on Apr. 19, 2024, 40 pages.
"Covid-19 Dashboard", Center for Systems Science and Engineering (CSSE), online available <https://www.arcgis.com/apps/dashboards/bda7594740fd40299423467b48e9ecf6>, retrieved on Apr. 19, 2024, p. 1.
New Hope", Senators propose mandatory listing of dietary supplements with FDA", Apr. 28, 2022, New Hope Network, 4 pages.
Wu et al., "Analysis of Therapeutic Targets for SARS-CoV-2 and Discovery of Potential Drugs by Computational Methods", Acta Pharmaceutica Sinica B, vol. 10, No. 5, 2020, pp. 766-788.
"Nutrient Recommendations: Dietary Reference Intakes (DRI)", National Institutes of Health, online available <https://ods.od.nih.gov/HealthInformation/nutrientrecommendations.aspx>, retrieved on Apr. 19, 2024, 6 pages.
"Water-Soluble Vitamins", 2nd National Report on Biochemical Indicators of Diet and Nutrition in the U.S. Population, 2012, pp. 13-84.
Singh et al., "Zinc for the Common Cold", Cochrane Database of Systematic Reviews, 2014, 93 pages.
Harokopakis et al., "Inhibition of Proinflammatory Activities of Major Periodontal Pathogens by Aqueous Extracts from Elder Flower (Sambucus Nigra)", Journal of Periodontology, vol. 77, No. 2, Feb. 2006, pp. 271-279.
"Cholecalciferol (Code C48194)", National Cancer Institute, Wikipedia, online available <https://ncithesaurus.nci.nih.gov/ncitbrowser/ConceptReport.jsp?dictionary=NCI_Thesaurus&ns=ncit&code=C48194>, retrieved on Apr. 19, 2024, 96 pages.
Dawson-Hughes et al., "Dietary Fat Increases Vitamin D-3 Absorption", Journal of the Academy of Nutrition and Dietetics, 2014, 6 pages.
Ting et al., "A Positive Feedback Signaling Loop Between ATM and the Vitamin D Receptor is Critical for Cancer Chemoprevention by Vitamin D", Cancer Research, vol. 72, No. 4, 2012, pp. 958-968.
"Hesperidin (HMDB0003265)", The Metabolomics Innovation Centre, Wikipedia, online available <https://hmdb.ca/metabolites/HMDB0003265>, retrieved on Apr. 19, 2024, 8 pages.
"Allicin (HMDB0033963)", The Metabolomics Innovation Centre, Wikipedia, online available <https://hmdb.ca/metabolites/HMDB0033963>, retrieved on Apr. 19, 2024, 18 pages.
"Osteoporosis Overview", National Institute of Arthritis and Musculoskeletal and Skin Diseases, online available <https://www.niams.nih.gov/health-topics/osteoporosis#:~:text=Overview%20of%20Osteoporosis,of%20fractures%20(broken%20bones).>, retrieved on Apr. 19, 2024, 7 pages.
"Green Tea", National Centre for Complementary and Integrative Health, online available <https://www.nccih.nih.gov/health/green-tea>, retrieved on Apr. 19, 2024, 6 pages.
Fact Sheet for Consumers, "Vitamin C", National Institutes of Health, Mar. 26, 2021, Wikipedia, online available <https://ods.od.nih.gov/factsheets/VitaminC-HealthProfessional/>, retrieved on Apr. 19, 2024, 30 pages.
Roh, Changhyun., "A Facile Inhibitor Screening of SARS Coronavirus N Protein Using Nanoparticle-based RNA Oligonucleotide", International Journal of Nanomedicine, vol. 7, 2012, pp. 2173-2179.
"Elderberry", National Centre for Complementary and Integrative Health, online available <https://www.nccih.nih.gov/health/elderberry#:~:text=Elderberry%20is%20the%20dark%20purple,%2C%20flu%2C%20and%20other%20conditions>, retrieved on Apr. 22, 2024, 4 pages.

* cited by examiner

| Active Ingredient | Chemical Structure |
|---|---|
| Ascorbic Acid (Vitamin C) | 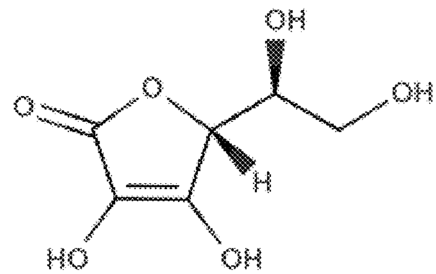 |
| Cholecalciferol (Vitamin D) | 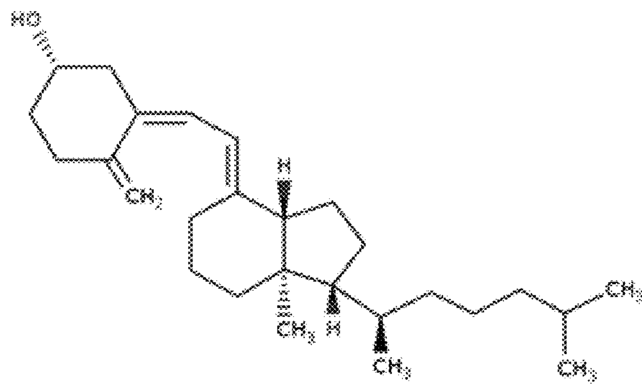 |
| Zinc Citrate Dihydrate | 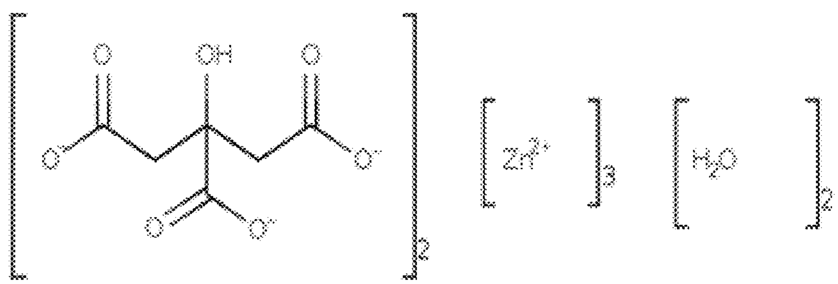 |
| Copper Gluconate | 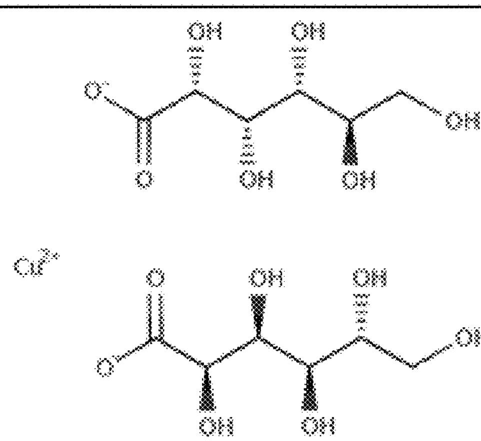 |

Table 100

FIG. 1

| Active Ingredient | Chemical Structure |
|---|---|
| Quercetin Dihydrate | 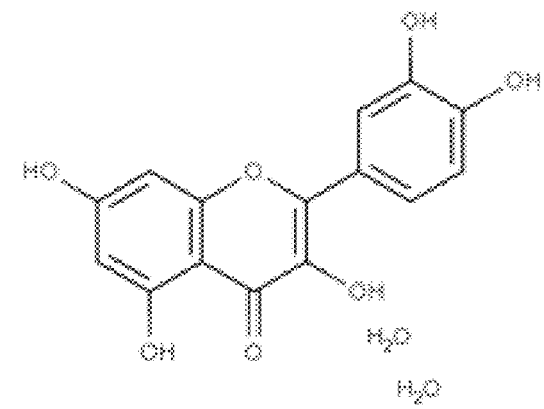 |
| Epigallocatechin gallate (EGCG) | 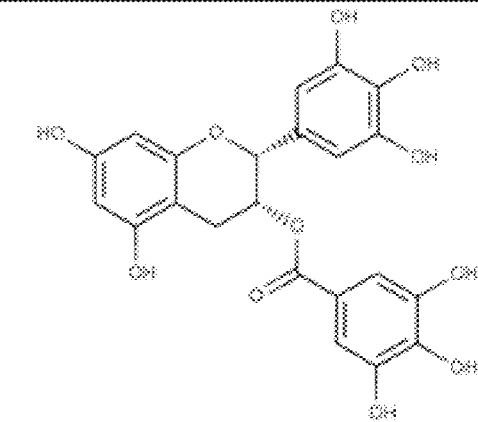 |
| Hesperidin | 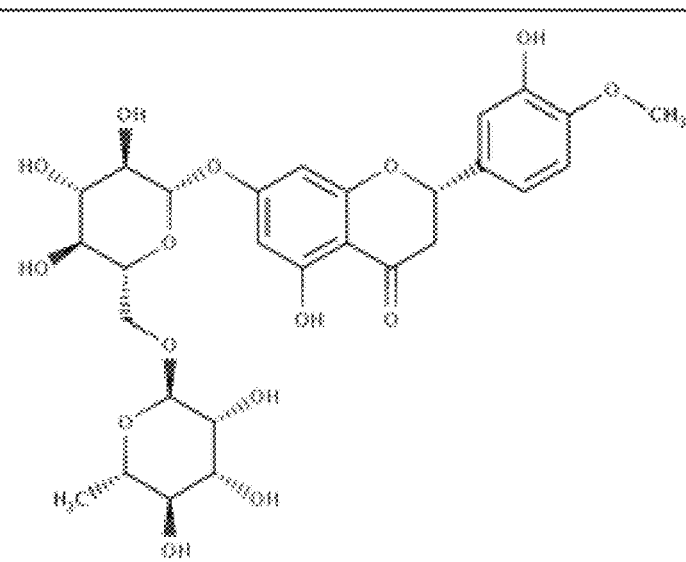 |
Table 100
(Continued)
FIG. 1

| Active Ingredient | Chemical Structure |
|---|---|
| Caffeic Acid | 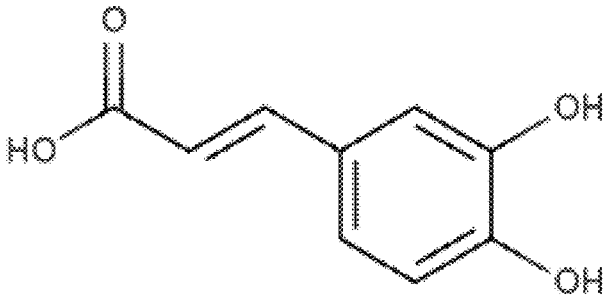 |
| Bovine Lactoferrin | 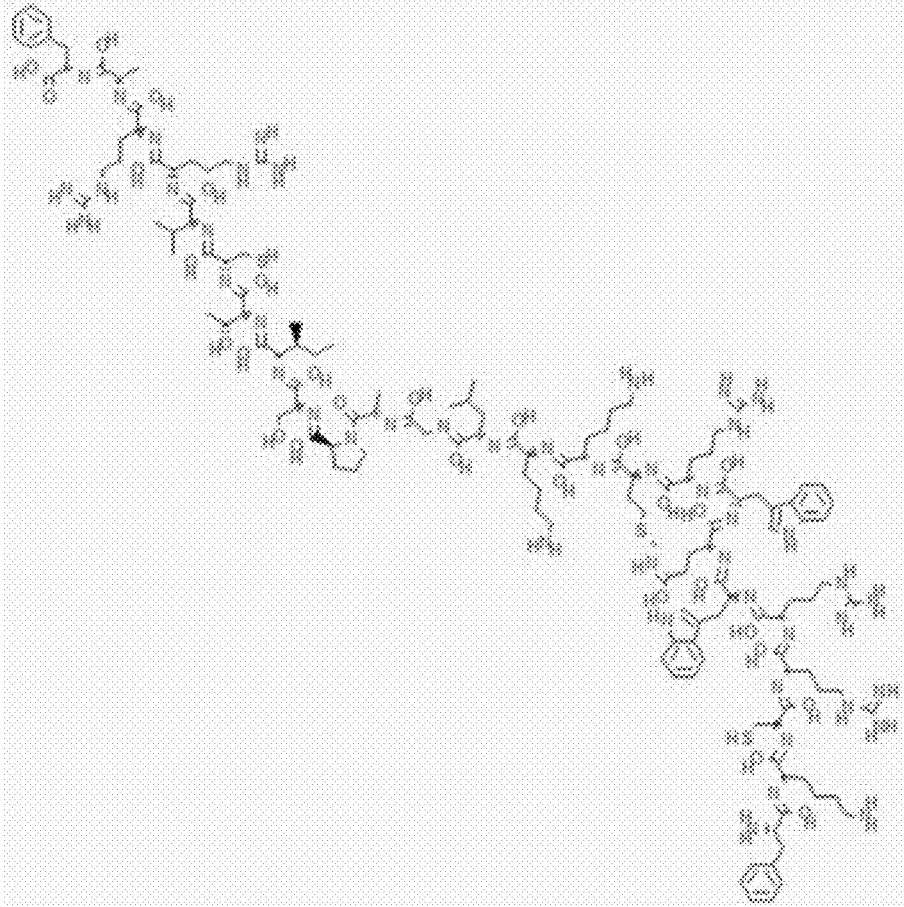 |
Table 100
(Continued)
FIG. 1

| Active Ingredient | Type of Action | Type of Evidence | Mechanisms of Action/Therapeutic Target |
|---|---|---|---|
| Ascorbic Acid | General | *In vivo* | Correction of micronutrient deficiencies in 7% of Americans overall, with a higher prevalence in the elderly |
| | Indirect | *In vivo* | Adaptive and Innate Immune Support |
| | | *In vitro* | Increases EGCG bioavailability (synergistic effect) |
| Cholecalciferol | General | *In vivo* | Correction of micronutrient deficiencies in 29% of Americans, with a higher prevalence in the elderly, obese and African Americans |
| | Indirect | *In vivo* | Immune System Modulation |
| Zinc Citrate Dihydrate | General | *In vivo* | Correction of micronutrient deficiencies in 10% of Americans, with a higher prevalence in the elderly |
| | Indirect | *In vivo* | Adaptive and Innate Immune Support |
| | Direct | *In vitro* | SARS-CoV-2 3CLpro, SARS-CoV-2 PLpro, and SARS-CoV-2 RdRp ($IC_{50}$ 1.3-1.4μM) |
| Copper Gluconate | Direct | *In vitro* | SARS-CoV-2 3CLpro |
| Quercetin Dihydrate | Direct | *In vitro* | SARS-CoV-2 3CLpro ($IC_{50}$ 73μM) |
| | | *In silico* | SARS-CoV-2 S-protein: ACE2 receptor interface |
| | Indirect | *In vivo* | Increases EGCG bioavailability (synergistic effect) |
| | | *In vitro* | Zinc Ionophore (synergistic effect) |

Table 300

FIG. 3

| Active Ingredient | Type of Action | Type of Evidence | Mechanisms of Action/Therapeutic Target |
|---|---|---|---|
| Epigallocatechin Gallate (EGCG) | Direct | In vitro | SARS-CoV-2 3CLpro (IC$_{50}$ 73.2µM) |
| | | In silico | SARS-CoV-2 PLpro |
| | | In vitro | SARS-CoV-2 3CLpro (IC$_{50}$ 0.847µM) |
| | | In vitro | Interference with heparan sulfate proteoglycans (EC50 0.1-1µM) |
| | Indirect | In vitro | Zinc Ionophore (synergistic effect) |
| | | In vitro | PLA2 Inhibition |
| Caffeic Acid | Direct | In vitro | Inhibition of human coronavirus NL63 (IC$_{50}$ 3.54µM) |
| | | In silico | SARS-CoV-2 M-protein, envelope, and nucleocapsid |
| | Indirect | In vivo | Inhibition of S-protein attachment |
| Hesperidin | Direct | In vitro | SARS-CoV-2 3CLpro via hesperetin (IC$_{50}$ 8.3µM) |
| | | In silico | SARS-CoV-2 S-protein: ACE2 receptor interface, Helicase, and 3CLpro |
| Bovine Lactoferrin | Direct | In vivo | Competitive inhibition of ACE2 receptors (IC$_{50}$ not listed) |
| | | In vitro | Competitive inhibition of heparan sulfate proteoglycans (IC$_{50}$ 0.7µM) |
| | Indirect | In vitro | Immunomodulatory regulation of pro-inflammatory cytokines |

Table 300
(Continued)

FIG. 3

| Active Ingredient | Type of Action | Type of Evidence | Mechanisms of Action/Therapeutic Target |
|---|---|---|---|
| Luteolin | General | *In silico* | SARS-CoV-2 S-protein: ACE receptor interface |
| | | *In vitro* | SARS-CoV-2 S protein S2 subunit (ECC$_{50}$ 10.6μM) |
| | | *In vitro* | SARS-CoV-2 3CLpro (IC$_{50}$ 20.2μM) |
| Myricetin | General | *In vitro* | SARS-CoV-2 Helicase (IC50 2.71μM) |
| | | *In vitro* | SARS-CoV-2 3CLpro (IC50 2.86μM) |
| Pomegranate Extract | General | *In vivo* | Correction of micronutrient deficiencies |
| | Indirect | *In vivo* | Adaptive and Innate Immune Support |
| Allicin | Indirect | *In vivo* | Adaptive and Innate Immune Support |
| Ginger | General | *In vivo* | Adaptive and Innate Immune Support |
| Elderberry Extract | Direct | *In vitro* | Inhibition of coronaviral replication and viral attachment via caffeic acid |

Table 400

FIG. 4

PHARMACOLOGICAL COMPOSITIONS FOR THE TREATMENT AND PREVENTION OF CORONAVIRUS DISEASE

RELATED APPLICATION

This application claims priority to U. S. Provisional Application Ser. No. 63/107,139 filed Oct. 29, 2020 and titled "PHARMACOLOGICAL COMPOSITIONS FOR THE TREATMENT AND PREVENTION OF CORONAVIRUS DISEASE," the entirety of which application is incorporated herein by reference.

TECHNICAL FIELD

This application relates to pharmacological compositions for the treatment and prevention of disease caused by a coronavirus, particularly the severe acute respiratory syndrome coronavirus 2 (SARS-CoV-2) and related viruses.

BACKGROUND

Starting in December 2019, a novel coronavirus, designated SARS-CoV-2 has caused an international and rapidly growing pandemic of respiratory illness termed COVID-19 (also referred to as coronavirus disease). The full spectrum of COVID-19 ranges from a mild, self-limiting respiratory disease course to severe progressive pneumonia, multiorgan failure, and death. Thus far, there are no specific therapeutic agents for coronavirus infections. In less than six months of the pandemic, there have been over four million people with a confirmed diagnosis of COVID-19 and over 300,000 deaths worldwide, with the United States being the worst affected country with over one million confirmed cases.

Healthcare systems around the world are becoming increasingly strained and there is currently a desperate need of a safe and effective treatment for COVID-19. As of May 2020, no effective treatment for COVID-19 exists and there are no antiviral drugs approved by the Food and Drug Administration (FDA) to prevent and treat patients with COVID-19. There are also currently no repurposed drugs approved by the FDA to treat patients with COVID-19. Current COVID-19 treatment guidelines from the Center for Disease Control (CDC) only provide for hospitalization for supportive management. The Infectious Diseases Society of America has also released seven guidelines for the management of COVID-19 patients. As of May 2020, six of the seven guidelines recommend using experimental drugs such as hydroxychloroquine, azithromycin, and others only when administered in the context of a clinical trial. The seventh recommendation discourages the use of corticosteroids.

SUMMARY

The following presents a summary to provide a basic understanding of one or more embodiments of the present disclosure. This summary is not intended to identify key or critical elements or to delineate any scope of the particular embodiments or any scope of the claims. Its sole purpose is to present concepts in a simplified form as a prelude to the more detailed description that is presented later. The disclosed subject matter is directed to pharmacological compositions for the treatment and prevention of COVID-19 and related diseases.

According to an embodiment, a composition for the treatment and prevention of disease caused by a coronavirus is provided, the composition having active ingredients comprising: ascorbic acid, cholecalciferol, zinc (as zinc citrate dihydrate or other forms of elemental zinc), copper (as copper gluconate or other forms of elemental copper), epigallocatechin gallate (or other flavonoids found within green tea), quercetin (as quercetin dihydrate or other forms of quercetin), hesperidin, caffeic acid, bovine lactoferrin and derivatives of these active ingredients. In some implementations, the active ingredients may further comprise one or more ingredients selected from the group consisting of: luteolin, myricetin, pomegranate extract, allicin, ginger, elderberry, and derivatives thereof. In various embodiments, the coronavirus comprises SARS-CoV-2 and derivatives thereof, and the composition is effective in treating and/or preventing coronavirus disease (COVID-19) in humans and other mammals.

According to another embodiment, a method for treating or inhibiting a disease in a patient caused by a virus is provided. The method comprises administering an effective amount of an antiviral composition to the patient, the antiviral composition having active ingredients comprising: ascorbic acid, cholecalciferol, zinc (as zinc citrate dihydrate or other forms of elemental zinc), copper (as copper gluconate or other forms of elemental copper), epigallocatechin gallate (or other flavonoids found within green tea), quercetin (as quercetin dihydrate or other forms of quercetin), hesperidin, caffeic acid, bovine lactoferrin and derivatives of the active ingredients. In various embodiments, the coronavirus comprises SARS-CoV-2 and derivatives thereof, and the composition is effective in treating and/or preventing coronavirus disease (COVID-19) in humans and other mammals.

In another embodiment, an antiviral composition is provided that serves a broad-spectrum antiviral therapeutic agent. The antiviral composition comprises two or more active ingredients selected from the group consisting of: ascorbic acid, cholecalciferol, zinc citrate dihydrate, copper gluconate, epigallocatechin gallate, quercetin dihydrate, hesperidin, caffeic acid, and bovine lactoferrin. In some implementations, the active ingredients may further comprise one or more ingredients selected from the group consisting of: luteolin, myricetin, pomegranate extract, allicin, ginger, elderberry, and derivatives thereof.

DESCRIPTION OF THE DRAWINGS

FIG. 1 provides a table identifying ingredients of one or more pharmacological compositions for treating and preventing disease caused by a coronavirus in accordance with one or more embodiments of the disclosed subject matter.

FIG. 3 provides provide another table describing antiviral mechanisms of different ingredients of one or more pharmacological compositions for treating and preventing disease caused by a coronavirus in accordance with one or more embodiments of the disclosed subject matter.

FIG. 4 provides another table describing antiviral mechanisms of some additional active ingredients of one or more pharmacological compositions for treating and preventing disease caused by a coronavirus in accordance with one or more embodiments of the disclosed subject matter.

DETAILED DESCRIPTION

Figure 2:
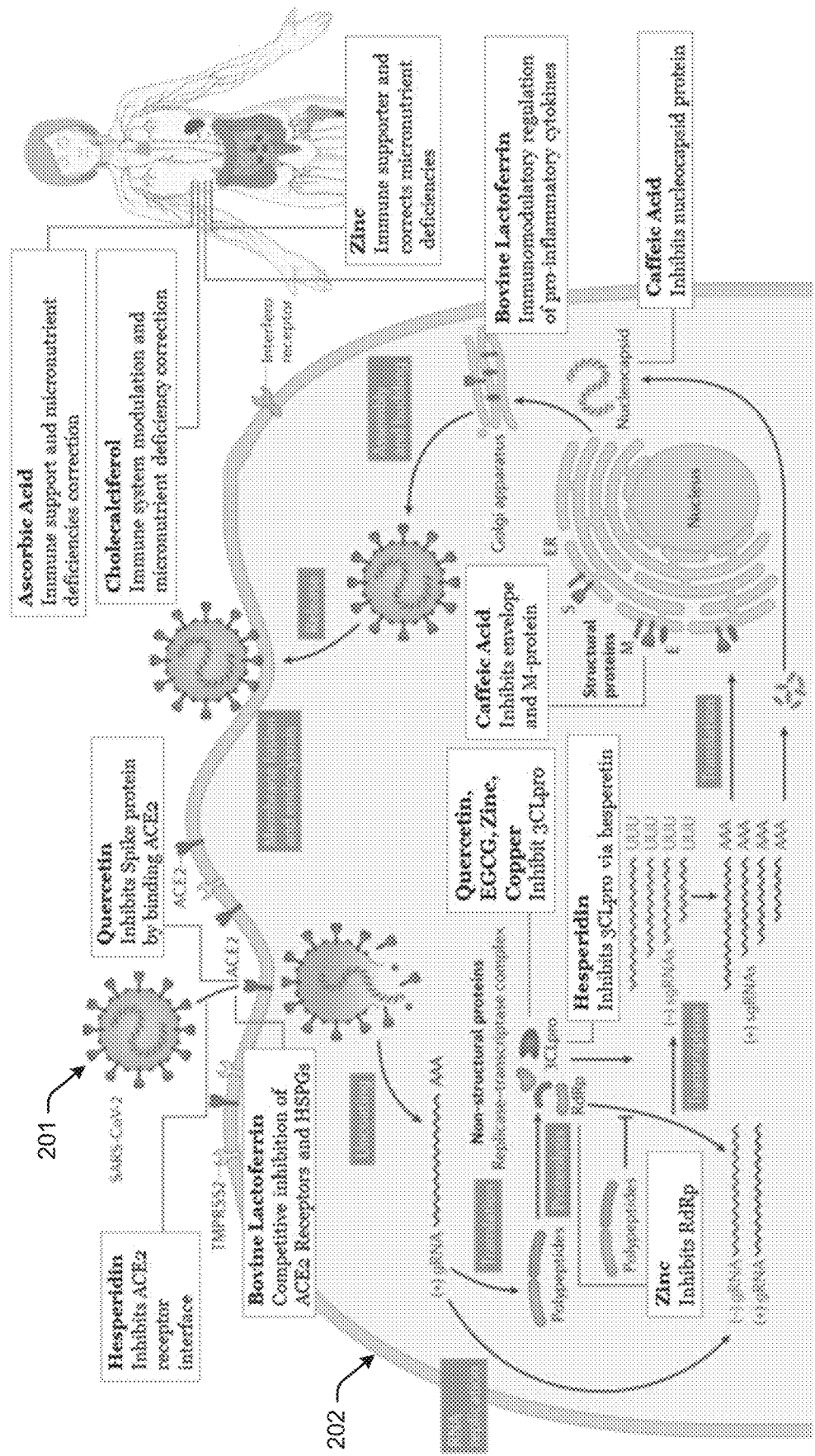
FIG. 2 illustrates the SARS-CoV-2 lifecycle within a human cell and the mechanisms of action of active ingredients of the disclosed pharmacological compositions in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Technical Field or Summary sections, or in the Detailed Description section.

The disclosed subject matter is directed to pharmaceutical compositions for the treatment and prevention of coronavirus disease (COVID-19) and related diseases. The disclosed pharmaceutical compositions can also provide broad spectrum antiviral activity against other viruses, including but not limited to, influenza virus, herpesvirus, cytomegalovirus, human immunodeficiency virus (HIV), and other viruses.

The pharmaceutical compositions employ unique combinations of vitamins, minerals, and botanicals and can be administered to patients using dosages easily achieved with ordinary food intake. In various embodiments, the active ingredients comprise ascorbic acid, cholecalciferol, zinc (as zinc citrate dihydrate or other forms of elemental zinc), copper (as copper gluconate or other forms of elemental copper), epigallocatechin gallate (or other flavonoids found within green tea), quercetin (as quercetin dihydrate or other forms of quercetin), hesperidin, caffeic acid, bovine lactoferrin and derivatives of the active ingredients. In some embodiments, the active ingredients can comprise different combinations of two or more the above noted active ingredients and derivatives thereof. The active ingredients the active ingredients may further comprise one or more ingredients selected from the group consisting of: luteolin, myricetin, pomegranate extract, allicin, ginger, elderberry, and derivatives thereof. The combinations of the specific ingredients employed in the antiviral compositions can result in multiple synergistic antiviral effects which have the potential to both prevent and treat COVID-19 with low or no toxicity in humans and other mammals.

The disclosed pharmaceutical compositions can also be used to treat and/or prevent mutations of SARS-CoV-2, other diseases caused by different types of coronaviruses, including severe acute respiratory syndrome (SARS) coronavirus, and related diseases. In some embodiments, the disclosed pharmaceutical compositions can also be used for the treatment and/or prophylaxis of other diseases and/or conditions that may be related to COVID-19, exacerbated by COVID-19, and/or that may make hosts more susceptible to more severe clinical complications of the disease, including but not limited to: chronic lung disease, asthma, heart disease, heart conditions, immune disorders, diabetes, kidney disease, liver disease, hemoglobin disorders, cancer and combinations thereof. In this regard, the disclosed compositions can be used as a broad-spectrum antiviral agent for the treatment and prevention of a variety of viruses.

Also provided are methods of treating and/or preventing disease caused by a coronavirus and other viruses in humans and other mammals. The methods typically involve administering one or more of dosages of the disclosed pharmaceutical compositions to the patient daily in an amount sufficient to inhibit growth and/or proliferation of the virus. In various embodiments, the pharmaceutical compounds can be administered orally (e.g., in the form of a capsule, pill, or the like), intravenously or in another suitable form. In certain embodiments the amount is an amount sufficient to exterminate or kill the virus. In some embodiments, the disclosed compositions can be administered to patients who have not contracted COVID-19 (or a related disease) to prevent contracting the disease. In other embodiments, the disclosed compositions can be administered to patients who have tested positive for COVID-19 (or a related disease) to treat the disease to minimize or eliminate the infection (e.g., to kill the virus) and/or to otherwise facilitate recovery from the disease.

The pharmaceutical compositions of the present invention may further comprise one or more pharmaceutically acceptable liquid or solid carriers as well as pharmaceutically acceptable additives. The disclosed pharmaceutical compositions can also be prepared using diluents or excipients such as fillers, extenders, binders, wetting agents, disintegrants, lubricants, surfactants, etc. that are commonly used in the preparation of medications and dietary supplements.

The solid form preparations may be tablets, pills, powders, granules, capsules, pellets, granules or powders, and such solid preparations may be prepared by adding a carrier, excipients and/or diluents to the compound. The carrier, excipient and/or diluent may include lactose, sucrose, dextrose, mannitol, malitol, sorbitol, xylitol, and erythritol. (erithritol), starch, acacia rubber, alginate, gelatin, calcium phosphate, calcium silicate, cellulose, polyvinyl pyrrolidone polyvinyl pyrrolidone, magnesium stearate, and mineral oil.

The formulations in liquid form may be solutions, suspensions or emulsions, and may include various excipients, for example wetting agents, sweeteners, fragrances, preservatives, etc., in addition to the commonly used simple diluents, water and liquid paraffin. Aqueous suspensions suitable for oral use may be prepared by dispersing the finely divided active ingredients in a viscous material such as natural or synthetic gums, resins, methyl cellulose, sodium carboxymethyl cellulose and known suspending agents.

Examples of fillers that can be used in the pharmaceutical compositions and dosage forms disclosed herein include talc, calcium carbonate (e.g., granules or powders), microcrystalline cellulose, powder cellulose, magnesium stearate, microcrystalline cellulose, dexrate, kaolin, mannitol, silicic acid, silica, sorbitol, Starch, pre-gelatin ring starch, and mixtures thereof, including but not limited to. The binder or filler of the disclosed pharmaceutical compositions can be generally present in suitable amounts (e.g., about 50 to about 99 weight percent of the pharmaceutical composition or dosage form).

Disintegrants that can be used in the pharmaceutical compositions and dosage forms disclosed herein are intended to disintegrate when the tablet is exposed to an aqueous environment. Tablets containing too much disintegrant may disintegrate during storage, while tablets containing too little do not disintegrate at the desired rate under the desired conditions. A sufficient amount of disintegrant, therefore not too much or too little, should not be used to form the solid oral dosage form of the invention so as not to be bad for controlling the release of the active ingredient. The amount of disintegrants used varies depending on the type of formulation and can be readily determined by one of ordinary skill in the art. Typical pharmaceutical compositions contain about 0.5 to about 15 weight percent of disintegrant, preferably about 1 to about 5 weight percent of disintegrant. Some example disintegrants that can be used in the disclosed antiviral compositions can include but are not limited to: agar, alginic acid, calcium carbonate, microcrystalline cellulose, croscarmellose sodium, crospovidone, poracryline potassium, sodium starch glycolenmit, potato or tapioca starch, other starch, pre-gelatinized starch, other starch, clay, other algins, other celluloses, gums, and mixtures thereof.

Glidants that can be used in the pharmaceutical compositions and dosage forms of the present invention are calcium stearate, magnesium stearate, mineral oil, light mineral oil, glycerin, sorbitol, mannitol, polyethylene glycol, other glycols, stearic acid, sodium Lauryl sulfate, talc, hydrogenated vegetable oils (e.g., peanut oil, cottonseed oil, sunflower oil, sesame oil, olive oil, corn oil, and soybean oil), zinc stearate, ethyl oleate, ethyl laurate, agar, and mixtures thereof. Additional lubricants are, for example, siloid silica (AEROSIL200, manufactured by WR Grace Co., Baltimore, MD), coagulated aerosol of synthetic silica, manufactured by Degussa Co., Plano, TX, CAB-O-SIL (pyrogenic silicon dioxide product, Cabot Co., Boston, Mass.), and mixtures thereof. If used, glidants are generally used in amounts up to about 1.0 percent weight t of the pharmaceutical composition or dosage form in which they are contained.

The pharmaceutical compositions of the present invention can be administered to mammals such as rats, mice, livestock, humans, etc. by various routes, and all modes of administration can be expected. For example, the compositions can be administered orally or parenterally, including by intravenous injection, subcutaneous injection, intramuscular injection, intraperitoneal injection, transdermal administration, intrauterine, epidural or intracerebroventricular injection, or the like. Examples of the parenteral administration include injections, drops, sap, ointments, sprays, suspensions, emulsions, suppositories, and the like. Formulations for parenteral administration include sterilized aqueous solutions, non-aqueous solutions, suspensions, emulsions, freeze-dried preparations and suppositories. As the non-aqueous solvent and suspending agent, propylene glycol, polyethylene glycol, vegetable oils such as olive oil, injectable esters such as ethyl oleate may be used. As a suppository base, witepsol, macrogol, tween 61, cacao butter, laurin butter, glycerogelatin, and the like may be used.

As used herein, the terms "treatment" and/or "inhibition" means obtaining the desired pharmacological and/or physiological effect. Such an effect may be a prophylactic effect in terms of completely or partially suppressing a disease or symptoms thereof and/or may be a therapeutic effect in terms of partially or fully curing the adverse effects caused by the disease and/or disease. The terms "treatment" and/or "inhibition" as used herein encompasses any treatment for diseases of mammals, particularly humans. The terms "treatment" and/or "inhibition" as used herein can refer to treating and/or inhibiting disease applied to subjects susceptible to the disease but not yet diagnosed as diseased; preventing the development of the disease; inhibiting the disease (e.g., arresting the onset of the disease); and/or alleviating the disease (e.g., causing regression of the disease).

The pharmaceutical compositions disclosed herein are intended to be administered in a therapeutically effective amount upon administration for clinical purposes. The term "therapeutically effective amount" means an amount sufficient to treat a disease at a reasonable benefit/risk ratio applicable to medical treatment, and the effective amount for a particular patient based on relevant patient variables (e.g., age, sex, weight, health status, medical history, comorbidities, underlying conditions, etc.), time of administration, route of administration, rate of excretion, active ingredient mixture and ratios, and severity of disease. However, for the desired effect, the one or more of the disclosed pharmaceutical compounds may be administered in an amount of 0.0001 to 1000 milligrams per kilogram (mg/kg) divided once or several times a day, and preferably in the form of a 750 mg capsule administered twice daily.

The amount of the active ingredients of the disclosed pharmaceutical compositions can be combined with a substance such as a carrier to produce a dosage form can vary depending upon the host to be treated and the particular mode of administration. The composition may contain from 0.001 to 95% of the active ingredients, and a typical pharmaceutical formulation may contain from about 5% to about 95% of the active ingredient (w/w). In another embodiment, the pharmaceutical formulations described herein may contain about 20% to about 80% active ingredients.

Those skilled in the art will readily understand that dosage levels may vary as a function of specific coronavirus inhibitory compounds, the severity of symptoms and the subject's susceptibility to side effects. Preferred dosages of pharmaceutical compositions comprising the active ingredients disclosed herein can be readily determined by one skilled in the art by a variety of means.

In many embodiments, multiple doses of the pharmaceutical compositions disclosed herein are administered to achieve the desired therapeutic effect. For example, about 1 week to about 2 weeks, about 2 weeks to about 4 weeks, about 1 month to about 2 months, about 2 months to about 4 months, about 4 months to about 6 months, about 6 months after virus exposure. In another embodiment, the disclosed pharmaceutical compositions can be administered once a month, twice a month, three times a month, over a period of about 8 months, about 8 months to about 1 year, about 1 year to about 2 years, about 2 years to about 4 years, or more. In another example embodiment, the pharmaceutical compounds disclosed herein can be administered every other week, once a week, twice a week, three times a week, four times a week, five times a week, six times a week, every other day, every day, twice a day or three times a day.

In many embodiments, the pharmaceutical compounds containing the active ingredients disclosed herein inhibit coronavirus replication. For example, the compounds of the present invention may inhibit coronavirus replication at least about 10%, at least about 15%, at least about 20%, at least about 25%, at least about 30%, as compared to coronavirus replication in the absence of the disclosed pharmaceutical compounds. In another embodiment, the disclosed pharmaceutical compounds can inhibit coronavirus replication by at least about 40%, at least about 50%, at least about 60%, at least about 70%, at least about 80%, or at least about 90% or more. Whether the compounds of the present invention inhibit coronavirus replication can be determined using methods known in the art, such as in vitro virus replication assays.

As used herein, the term "coronavirus" includes any member of the family of coroniviridae, including but not limited to any member of the genus Coronavirus and/or any member of the genus Torovirus. Coronaviridae is a family of viruses characterized by irregular shaped particles of 60-220 nanometers (nm) in diameter with a distinctive club-shaped perfluorometer with an envelope on the outside, which gives the virus a crown-like appearance. Coronoviridae includes the genus Coronavirus and Toro virus. Coronaviruses include infectious bronchitis virus (IBV), bovine coronavirus (BCoV), bat coronavirus BatCoV RaTG13, canine coronavirus (CCoV), feline coronavirus (FeCoV), porcine erythrocyte aggregated encephalomyelitis virus (PEDV), mouse hepatitis virus (MHV), and turkey coronavirus (TCoV), infectious gastrointestinal virus (TGEV), rat coronavirus (RCV), human coronavirus 229E (HCoV-229E), human coronavirus NL63 (NL), human coronavirus OC43 (HCoV-OC43), SARS coronavirus (SARS-CoV), SARS-CoV-2, and the like, but is not limited thereto. Toro viruses include, but are not limited to, Berne virus and Breda virus.

The present invention provides a pharmaceutical composition for the treatment and prevention of diseases caused by any one of the coronaviruses, and preferably provides a pharmaceutical composition for the treatment and prevention COVID-19 caused by SARS-CoV-2 coronavirus. The disclosed pharmaceutical compositions can also provide broad spectrum antiviral activity against other viruses, including but not limited to, influenza virus, herpesvirus, cytomegalovirus, HIV, and other viruses.

Further, the term "coronavirus" includes naturally occurring (e.g., wild type) coronaviruses, naturally occurring coronavirus variants, variants generated by selection, variants generated by chemical modifications, genetically modified variants (e.g., coronaviruses modified by recombinant DNA methods in the laboratory) and include laboratory generated coronavirus variants.

The term "specificity" when used with respect to antiviral activity of the disclosed pharmaceutical compounds indicates that the compound preferentially inhibits growth and/or proliferation and/or exterminates a particular virus as compared to mammalian red blood cells (RBCs). In certain embodiments the preferential inhibition or exterminate is at least 10% greater (e.g., the $LD_{50}$ being 10% lower), preferably at least 20%, 30%, 40%, or 50%, more preferably at least 2-fold, at least 5-fold, or at least 10-fold greater for the target virus.

The term "high" as used with respect to antiviral activity and/or potency is used herein to indicate that the level of antiviral activity of an antiviral compound disclosed herein is greater than a defined minimum threshold of antimviral activity or potency for a particular coronavirus. In various embodiments, the minimum threshold can be based on its minimum inhibitory concentration (MIC), its $LD_{50}$ concentration/or its $HC_{50}$, concentration, wherein the lower the concentration, the higher the antiviral activity and/or potency. For example, in some embodiments, an antiviral composition disclosed herein can be considered to have high antiviral activity and/or potency if its MIC is less than 250 micrograms per milliliter (μg/mL), more preferably less than 150 μg/mL, more preferably less than 100 μg/mL, more preferably less than 50 μg/mL, and even more preferably less than 30 μg/mL.

The term "low-toxicity" is used herein to indicate any level of toxicity of a pharmacological composition that is less than defined acceptable threshold of toxicity. In various embodiments, the defined threshold can be based on the MIC of the pharmacological composition relative to its $LD_{50}$ and/or $HC_{50}$ concentration. In some implementations, a pharmacological composition disclosed herein can be considered to have low-toxicity if its MIC is less than its $LD_{50}$ and/or $HC_{50}$ concentration. In other implementations, a pharmacological composition can be considered to have low-toxicity if its MIC is 60% or less than its $LD_{50}$ and/or $HC_{50}$ concentration. In other implementations, a pharmacological composition can be considered to have low-toxicity if its MIC is 50% or less than its $LD_{50}$ and/or $HC_{50}$ concentration. In other implementations, a pharmacological composition can be considered to have low-toxicity if its MIC is 30% or less than its $LD_{50}$ and/or $HC_{50}$ concentration. In other implementations, a pharmacological composition can be considered to have low-toxicity if its MIC is 25% or less than its $LD_{50}$ and/or $HC_{50}$ concentration.

One or more embodiments are now described with reference to the drawings, wherein like reference numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details. It is noted that the drawings of the present application are provided for illustrative purposes only and, as such, the drawings are not drawn to scale.

FIG. 1 provides a table (Table 100) identifying ingredients of one or more pharmacological compositions for treating and preventing disease caused by a coronavirus in accordance with one or more embodiments of the disclosed subject matter. The pharmacological compositions comprising the active ingredients listed in Table 100 can also function as broad-spectrum antiviral agents for the treatment and prevention of other viral diseases. Table 100 lists nine different active ingredients that can be included in one or more pharmaceutical compositions for the treatment and/or prevention of disease caused by a coronavirus (e.g., SARS-COV-2) and other viruses. These ingredients include ascorbic acid, cholecalciferol, zinc (as zinc citrate dihydrate or other forms of elemental zinc), copper (as copper gluconate or other forms of elemental copper), epigallocatechin gallate (or other flavonoids found within green tea), quercetin (as quercetin dihydrate or other forms of quercetin), hesperidin, caffeic acid, bovine lactoferrin and derivatives of the active ingredients. Table 100 further provides the chemical structures of the active ingredients.

In some embodiments, an effective pharmacological composition for the treatment and/or prevention of diseases (e.g., COVID-19) caused by and/or exacerbated by a coronavirus (e.g., SARS-CoV-2 and related viruses) can comprise effective amounts of all nine ingredients listed in Table 100 (or derivatives thereof). The active ingredients can be combined for example in a pill or capsule and administered orally. According to these embodiments, per single unit (e.g., single capsule, pill or another form), the pharmacological composition can comprise the following amounts of the respective active ingredients: about 30.0 milligrams (mg) to about 120 mg of ascorbic acid, more preferably about 50.0 mg to about 100 mg of ascorbic acid, even more preferably about 60.0 mg to about 80.0 mg of ascorbic acid; about 5.0 micrograms (μg) to about 50.0 μg of cholecalciferol, more preferably about 10.0 μg to about 40 μg of cholecalciferol, and even more preferably about 15.0 μg to about 25.0 μg of cholecalciferol; about 0.5 mg to about 20 mg of zinc, more preferably, about 1.0 mg to about 15.0 mg of zinc, and even more preferably about 3.0 mg to about 7.0 mg of zinc; about 0.05 mg to about 5.0 mg of copper, more preferably about 0.1 mg to about 2.0 mg of copper, and even more preferably about 0.15 mg to about 1.0 mg of copper; about 10.0 mg to about 100 mg of epigallocatechin gallate (EGCG), more preferably about 30.0 mg to about 80.0 mg of EGCG, and even more preferably about 40.0 mg to about 60.0 mg of EGCG; about 50.0 mg to about 150 mg of quercetin, more preferably about 70.0 mg to about 130 mg of quercetin, and even more preferably about 80.0 mg to about 100 mg of quercetin; about 30.0 mg to about 120 mg of hesperidin, more preferably about 50.0 mg to about 100 mg of hesperidin, even more preferably about 60.0 mg to about 80.0 mg of hesperidin; about 10.0 mg to about 100 mg of caffeic acid, more preferably about 30.0 mg to about 80.0 mg of caffeic acid, and even more preferably about 40.0 mg to about 60.0 mg of caffeic acid; about 10.0 mg to about 100 mg of bovine lactoferrin, more preferably about 30.0 mg to about 80.0 mg of bovine lactoferrin, and even more preferably about 40.0 mg to about 60.0 mg of bovine lactoferrin.

The above noted amounts of the active ingredients correspond the amounts of the respective active ingredients per unit of the pharmacological composition. In this regard, it should be appreciated that the composition can be discretized into units (e.g., encapsulated units, or another form), and wherein each unit (e.g., each capsule, pill, etc.) comprises the active ingredients in accordance with one or more of the above noted amounts. In accordance with these amounts, the effective dose can range between one and ten units per day, which can vary based on the patient (with respect to patient condition, age, weight, comorbidities, etc.) and the amounts of the active ingredients included in each unit. For example, in some implementations, the effective dose may include two to four units daily. In other implementation, the effective dose may include three to six units daily (e.g., three units taken twice daily).

For instance, in accordance with one example implementation, each unit (e.g., each capsule) comprises about 30.0 mg to about 120 mg of ascorbic acid, about 5.0 μg to about 50.0 μg of cholecalciferol, about 0.5 mg to about 20 mg of zinc, about 0.05 mg to about 5.0 mg of copper, about 10.0 mg to about 100 mg of epigallocatechin gallate, about 50.0 mg to about 150 mg of quercetin, about 30.0 mg to about 120 mg of hesperidin, about 10.0 mg to about 100 mg of caffeic acid, and about 10.0 mg to about 100 mg of bovine lactoferrin, and the effective dose comprises between one and ten units per day, more preferably, two to four units per day, and even more preferably three to six units per day.

In other implementation, each unit (e.g., each capsule) comprises about 50.0 mg to about 100 mg of ascorbic acid, about 10.0 m to about 40.0 m of cholecalciferol, about 1.0 mg to about 15 mg of zinc, about 0.1 mg to about 2.0 mg of copper, about 30.0 mg to about 80 mg of epigallocatechin gallate, about 70.0 mg to about 130 mg of quercetin, about 50.0 mg to about 100 mg of hesperidin, about 30.0 mg to about 80 mg of caffeic acid, and about 30 mg to about 80 mg of bovine lactoferrin, and the effective dose comprises between one and ten units per day, more preferably, two to four units per day, and even more preferably three to six units per day.

In other implementation, each unit (e.g., each capsule) comprises about 60 mg to about 80 mg of ascorbic acid, about 15.0 m to about 25.0 μg of cholecalciferol, about 3.0 mg to about 7 mg of zinc, about 0.15 mg to about 1.0 mg of copper, about 40.0 mg to about 60 mg of epigallocatechin gallate, about 80.0 mg to about 100 mg of quercetin, about 60.0 mg to about 80 mg of hesperidin, about 40.0 mg to about 60 mg of caffeic acid, and about 40 mg to about 60 mg of bovine lactoferrin, and the effective dose comprises between one and ten units per day, more preferably, two to four units per day, and even more preferably three to six units per day.

In another embodiment, an effective pharmacological composition for the treatment and/or prevention of diseases (e.g., COVID-19) caused by and/or exacerbated by a coronavirus (e.g., SARS-CoV-2 and related viruses) can comprise a subset of the nine active ingredients listed in Table 100. For example, in some embodiments, the pharmacological composition can comprise eight, seven, six, five, four, three or only two of the active ingredients listed in Table 100. For example, in some embodiments, copper and/or zinc may be removed from the composition yet still provide antiviral and other therapeutic effect for patients with sensitivity to zinc and/or copper. According to these embodiments, the amounts of the respective ingredients as included in the pharmacological composition can adhere to the ranges and amounts described above.

The combination of the specific ingredients employed in the subject pharmaceutical compositions can result in multiple synergistic antiviral effects which have the potential to both prevent and treat COVID-19 with low or no toxicity in humans and other mammals. In this regard, the pharmaceutical compositions described herein can treat and inhibit infection of SARS-CoV-2 and other coronaviruses in human cells using different mechanisms of action attributed to one or more synergistic combinations of the active ingredients listed in Table 100.

Severe acute respiratory syndrome coronavirus 2 (SARS-CoV-2) is a positive-sense single-stranded RNA virus, contagious in humans and spread via close contact and via respiratory droplets from coughs or sneezes. The genome of SARS-CoV-2 consists of approximately 29700 nucleotides, about 80% and 96% identical to the SARS-CoV and the bat coronavirus BatCoV RaTG13 genomes, respectively. SARS-CoV-2 has four structural proteins, known as the spike protein (also referred to as the S protein), the envelope protein (also referred to as the E protein), the membrane protein (also referred to as the M protein), and the nucleocapsid protein (also referred to as the N protein). The N protein holds the RNA genome, and the S, E, and M proteins together create the viral envelope.

The disclosed pharmaceutical compositions target multiple areas of the coronavirus via both direct and indirect antiviral actions. In various embodiments, the disclosed compositions can treat and inhibit infection of the virus in human cells based on direct or indirect disruption of one or more biological targets of the coronavirus caused by one or more of the active ingredients, wherein the one or more biological targets are selected from a group consisting of: spike protein, helicase (nsp13), RNA-dependent RNA polymerase (RdRp), propapain-like protease (PLpro), and chymotrypsin-like protease (3CLpro).

The spike protein allows the SARS-CoV-2 virus to attach to and fuse with the membrane of a host cell by binding to the angiotensin converting enzyme 2 (ACE2) receptor. As described in greater detail below, one or more of the active ingredients included in Table 100 can directly or indirectly interfere with the spike protein and ACE2 receptor interaction to prevent or minimize binding of the SARS-CoV-2 virus (and related viruses) with the ACE2 receptor of the host cell.

Helicase, also known as Nsp13, is a multi-functional protein with an N-terminal metal binding domain and helicase domain and is a necessary component for the replication of coronavirus. Helicase inhibition would also therefore help block viral replication.

RdRp, also known as nsp12, is a non-structural protein that is required for SARS-CoV-2 replication. The overall architecture of the COVID-19 virus nsp12-nsp7-nsp8 complex is similar to that of SARS-CoV with a root-mean-square deviation value of 0.82.

PLpro is responsible for the cleavages of N-terminus of the replicase poly-protein to release Nsp1, Nsp2 and Nsp3, which is essential for correcting SARS-CoV-2 replication.

3CLpro is the main protease in SARS-CoV-2 and is essential for processing the polyproteins that are translated from viral RNA. Inhibition of 3CLpro production would help block viral replication. By sequence alignment (as shown below), the SARS-CoV-2 and SARS-CoV 3CLpro genes share a remarkable 96% sequence identity (their corresponding proteins only differ by 12 amino acids), and the crystal structure of SARS-CoV-2 3CLpro is highly similar to its SARS sister (PDB ID: 2DUC) with very similar binding sites.

The disclosed anti-coronavirus compositions contain multiple ingredients found in nature. The rationale for the use of multiple ingredients and dosages in the disclosed compositions as opposed to using a single agent alone are numerous.

Firstly, the disclosed compositions are designed to be safe for use in humans and other mammals. The ingredients listed in Table 100 are a combination of micronutrients and flavonoids that are well tolerated, well-studied, and are either found in common foods or have a long safety history in human consumption. All of the dosages of the specific ingredients in the disclosed compositions are all within the upper tolerable safety limits set by the United States Institute of Medicine. The tolerable upper limit (UL) is defined by the United States Institute of Medicine as the maximum daily intake level at which no risk of adverse health effects is expected for almost all individuals in the general population, including sensitive individuals, when the nutrient is consumed over long periods of time. In other words, the UL is the highest usual intake level of a nutrient that poses no risk of adverse effects.

Secondly, the combination of the specific ingredients in the disclosed pharmaceutical compositions provide for both the correction of inadequate dietary intake of vitamins and minerals as well as antiviral treatment. Mortality from COVID-19 may be increased because of inadequate vitamin levels. Many individuals found to be more susceptible to COVID-19 are deficient in Vitamin D, Vitamin C, and zinc. Including these vitamins in the disclosed anti-coronavirus compositions allows for potential correction of these levels to adequate levels while also providing potential antiviral treatment.

Thirdly, specific ingredients in the disclosed pharmaceutical compositions may provide multiple synergistic effects. There are multiple synergistic effects for these ingredients in combination. For example, the use of zinc with quercetin and EGCG provides a synergistic response in both quercetin and EGCG may act as a zinc ionophore.

Fourthly, the use of multiple ingredients in the disclosed compositions may provide additive effects to overcome inadequate concentrations. Inhibition of SARS-CoV-2 infection is dependent on the plasma concentrations of the inhibitors. Given that the disclosed antiviral compositions have been formulated, first and foremost, to be safe at the intended administered dosage (as mentioned above), single ingredients within the disclosed antiviral compositions alone may not be sufficient to significantly inhibit the coronavirus. However, an additive effect to strongly suppress the virus could be potentially achieved with these ingredients together as many of them target the same enzyme/proteins.

In addition, thus use of multiple ingredients allows for multiple direct and indirect antiviral mechanisms of action against SARS-CoV-2. SARS-CoV-2 has multiple different virulence factors, each of which are potential targets for effective therapy. The use of multiple ingredients in the disclosed compositions allows for the simultaneous use of multiple potential mechanisms of action against SARS-CoV-2 and related viruses.

Furthermore, the use of multiple ingredients provides for potential maintained efficacy despite potential SARS-CoV-2 resistance mutations. In ordinary models of viral evolution, antiviral treatments that are only partially effective may result in a rapid adaptation toward resistance. This can be exacerbated by the large population sizes and high rates of mutation characterizing many viruses. Multiple mutations of the SARS-CoV-2 virus have already been discovered, and mutagenicity within the SARS-CoV-2 genome can potentially lead to reduced efficacy of a single agent over time as well as a general increase in viral resistance. Thus, the use of multiple ingredients in the disclosed anti-coronavirus medications allows for the simultaneous use of differing potential antiviral mechanisms of action against SARS-CoV-2, potentially reducing the risk of the development of resistance mutations in SARS-CoV-2.

FIG. 2 illustrates the lifecycle of the SARS-CoV-2 virus 201 within a human cell 202 and the mechanisms of action of active ingredients of the disclosed pharmacological compositions in accordance with one or more embodiments of the disclosed subject matter. The mechanisms of action of each of the nine active ingredients listed in Table 100 are overlaid onto relevant portions of the image to provide a graphical representation of the multiple mechanisms of action of the disclosed antiviral compositions against SARS-CoV-2. As illustrated in FIG. 2, hesperidin, bovine lactoferrin and quercetin provide collective combative mechanisms for inhibiting the binding of the virus to the cellular wall, thereby inhibiting translocation of the virus through the cell wall. Zinc inhibits SARS-CoV-2 3CL protease (3CLpro), papain-like protease 2 (PLP2), and RNA-dependent RNA polymerase (RdRp) activities, thereby inhibiting replication of the virus after entry into the cell. Zinc also provides immune support and corrects micronutrient deficiencies. The combination of hesperidin, quercetin, EGCG, zinc and copper further inhibit 3CLpro. Caffeic acid inhibits envelop and M-protein production by the virus as well as inhibiting production of the nucleocapsid protein by the virus. Bovine lactoferrin provides immunomodulatory regulation of pro-inflammatory cytokines. Finally, ascorbic acid and cholecalciferol bother provide immune support and/or modulation and correct micronutrient deficiencies.

FIG. 3 provides another table (Table 300) describing antiviral mechanisms of different ingredients of one or more pharmacological compositions for treating and preventing disease caused by a coronavirus in accordance with one or more embodiments of the disclosed subject matter.

With reference to FIG. 3A, ascorbic acid (also known as vitamin C) used in combination with one or more other ingredients listed in Table 300 facilitates treatment and prevention of COVID-19 and related diseases generally via general correction of micronutrient deficiencies and indirectly via adaptive and innate immune support, both of which mechanisms have been demonstrated in vivo. The overall prevalence of age-adjusted vitamin C deficiency was 7.1+/−0.9%, with an increasing prevalence in those with a lower socioeconomic status and smokers in the National Health and Nutrition Examination Survey 2003-2004 (NHANES). A history of vitamin C supplement usage or adequate dietary intake significantly decreased the risk of vitamin C deficiency (p<0.05). Vitamin C further indirectly fights against COVID-19 via replenishing Vitamin C reserves during active infection. Treatment of established infections requires significantly higher doses of Vitamin C to compensate for the increased inflammatory response and metabolic demand. Elderly hospitalized patients with acute respiratory infections have been shown to fare significantly better with vitamin C supplementation than those not receiving the vitamin C, and hospitalized patients, in general, have lower vitamin C status than the general population.

Vitamin C further increases EGCG bioavailability, thus providing a synergistic effect when combined with EGCG. In this regard, vitamin C enhances absorption of the EGCG when both are included in the disclosed pharmacological compositions. In vitro studies have demonstrated that vitamin C significantly increases absorption of EGCG. EGCG is a component of the STRI Formula which has direct effects on SARS-CoV-2.

Vitamin C is an essential micronutrient for humans, with pleiotropic functions related to its ability to donate electrons. It is a potent antioxidant and a cofactor for a family of biosynthetic and gene regulatory enzymes. Vitamin C contributes to immune defense by supporting various cellular functions of both the innate and adaptive immune system. Vitamin C accumulates in phagocytic cells, such as neutrophils, and can enhance chemotaxis, phagocytosis, generation of reactive oxygen species, and ultimately microbial killing. Vitamin C is required for the maturation of T lymphocytes, blood cells that help protect the body from infection. Vitamin C accumulates in neutrophils, or white blood cells, and facilitates their movement as they kill pathogens. In vitro, exogenous vitamin C has been shown to increase the number, proliferation, and function of T lymphocytes. Vitamin C deficiency can result in impaired immunity and higher susceptibility to infections. In turn, infections significantly impact on vitamin C levels, and the presence of active infection can also potentially further lower vitamin C levels as immune cells increase their use of vitamin C during the inflammatory process. This can become a vicious cycle of sickness and nutrient deficiency. Furthermore, supplementation with vitamin C appears to be able to both prevent and treat respiratory and systemic infections. Prophylactic prevention of infection requires dietary vitamin C intakes that provide at least adequate, if not saturating plasma levels (i.e., 100-200 mg/day), which optimize cell and tissue levels. In contrast, treatment of established infections requires significantly higher doses of the vitamin to compensate for the increased inflammatory response and metabolic demand. Furthermore, supplementation with vitamin C appears to be able to both prevent and treat respiratory and systemic infections. Prophylactic prevention of infection requires dietary vitamin C intakes that provide at least adequate, if not saturating plasma levels (i.e., 100-200 mg/day), which optimize cell and tissue levels. In contrast, treatment of established infections requires significantly higher (gram) doses of the vitamin to compensate for the increased inflammatory response and metabolic demand.

Lower vitamin C levels are also associated with all-cause mortality and elderly patients with respiratory infections fare better with exogenous vitamin C supplementation. A lower mean vitamin C status has been observed in free-living or institutionalized elderly people, indicated by lowered plasma and leukocyte concentrations, which is of concern because low vitamin C concentrations (<17 μmol/L) in older people (aged 75-82 years) are strongly predictive of all-cause mortality. Acute and chronic diseases that are prevalent in this age group may also play an important part in the reduction of vitamin C reserves. Institutionalization in particular is an aggravating factor in this age group, resulting in even lower plasma vitamin C levels than in non-institutionalized elderly people. It is noteworthy that elderly hospitalized patients with acute respiratory infections have been shown to fare significantly better with vitamin C supplementation than those not receiving the vitamin. Hospitalized patients, in general, have lower vitamin C status than the general population.

Vitamin C has also been shown to help strengthen pulmonary innate immunity in vitro. Vitamin C stimulates repair of the alveolar epithelial lining surface, damaged in acute lung injury caused by sepsis in mice. This protective mechanism in the lung alveolar epithelial surface was shown to be related to ascorbic acid's ability to stimulate the rebuilding of cellular tight junctions.

Similar to vitamin C, cholecalciferol (also known as vitamin D3) used in combination with one or more other ingredients listed in Table 200 facilitates treatment and prevention of COVID-19 and related diseases indirectly via correction of micronutrient deficiencies and immune system modulation. The groups with the highest levels of vitamin D deficiency are the same groups that are at higher risk for COVID-19. In vitro studies have demonstrated that administering vitamin D reduces the expression of pro-inflammatory cytokines and increases the expression of anti-inflammatory cytokines by macrophages.

Vitamin D deficiency (VDD) and insufficiency (VDI) are increasing at a global level, and they are associated with increased risk of various diseases. Low vitamin D levels have been found to correlate with higher rates of COVID-19 infection. The mean level of vitamin D3 (average 56 mmol/L, STDEV 10.61) in each country affected by COVID-19 was strongly associated with the number of cases/1M (mean 295.95, STDEV 298.73 $p=0.004$, respectively with the mortality/1M (mean 5.96, STDEV 15.13, $p<0.00001$). In addition, the nations with the highest mortality rates (including Italy, Spain and France) also had the lowest average vitamin D3 levels among countries affected by the pandemic. Zinc (as zinc citrate and other forms of zinc) facilitates treatment and prevention of COVID-19 and related diseases by directly inhibiting 3CLpro, PLpro and RdRp. Zinc ions have been found to inhibit SARS-CoV 3CLpro in vitro, which shares significant sequence homology with SARS-CoV-2 3CLpro. Zinc citrate also appears to inhibit PLpro in SARS-CoV which is similar homology to SARS-CoV-2. In addition, zinc citrate inhibits RdRp in SARS-CoV which shares homology to SARS-CoV-2. Positive zinc ions have further been found in vitro to inhibit SARS-CoV replication through direct inhibition of SARS-CoV RdRp.

Vitamin D3 can reduce the cytokine storm induced by the innate immune system as well as regulate adaptive immunity. The innate immune system generates both pro-inflammatory and anti-inflammatory cytokines in response to viral and bacterial infections, as observed in COVID-19 patients. Vitamin D3 can reduce the production of pro-inflammatory Th1 cytokines, such as tumor necrosis factor $\alpha$ and interferon $\gamma$. Vitamin D3 also suppresses responses mediated by the T helper cell type 1 (Th1), by primarily repressing production of inflammatory cytokines IL-2 and interferon gamma (INF$\gamma$) as has been previously shown.

Zinc used in combination with one or more other ingredients listed in Table 300 further facilitates treatment and prevention of COVID-19 and related diseases generally and indirectly by providing correction of micronutrient deficiencies and immune support. Zinc has significant effects on immune function. Zinc ions are involved in regulating intracellular signaling pathways in innate and adaptive immune cells. Zinc is essential for the immune system and elderly people have an increased probability for zinc deficiency, documented by a decline of serum or plasma zinc levels with age. Although most healthy elderly are not classified as clinically zinc deficient, even marginal zinc deprivation can affect immune function. Several striking similarities in the immunological changes during aging and zinc deficiency, including a reduction in the activity of the thymus and thymic hormones, a shift of the T helper cell balance towards TH2, decreased response to vaccination, and impaired functions of innate immune cells indicate that a wide prevalence of marginal zinc deficiency in elderly people may contribute to immunosenescence. Studies with oral zinc supplementation show the potential to improve the immune response of elderly people by restoration of the zinc levels, showing that balancing the zinc status may be a way to healthy aging.

Zinc further facilitates treatment and prevention of COVID-19 and related diseases generally directly by reacting with multiple biological targets of COVID-19. In particular, zinc citrate directly inhibits 3CLpro, PLpro, and RdRp. Zinc ions can inhibit SARS-CoV 3CLpro in vitro, which shares significant sequence homology with SARS-CoV-2 3CLpro. Zinc ions can also inhibit SARS-CoV PLpro in vitro which shares significant sequence homology with SARS-CoV-2 PLpro. Zinc ions further inhibit SARS-CoV in vitro via replication through direct inhibition of SARS-CoV RdRp. SARS-CoV-2 RdRp shares 96.4% genetic homology with SARS-CoV RdRp using standard BLAST reference homology comparisons.

Copper is an essential trace mineral that is not endogenous in humans and must be obtained through diet or supplementation. The disclosed antiviral compositions can include low (e.g., preferably less than 1.0 mg and more preferably less than 0.5 mg) of copper (as copper gluconate) per capsule. The inclusion of copper gluconate, an orally bioavailable copper salt of D-gluconic acid, provides copper supplementation to maintain zinc-copper homeostasis. However, the primary pharmacodynamic effects of copper gluconate as included withing the disclosed antiviral compositions include the inhibition of SARS-CoV-2 3CL protease activity and the exertion of antiviral effects during viral replication.

Quercetin directly facilitates treatment and prevention of COVID-19 and related diseases by directly inhibiting 3CLpro production and also by directly binding to the viral S protein, thereby inhibiting the S protein from binding to the human ACE2 receptor interface. Quercetin inhibits the 3C-like protease (3CLpro) (in vitro) of SARS-CoV using recombinant 3CLpro expressed in *Pichia pastoris* GS115. As described earlier, SARS-CoV-2 3CLpro has extensive protein structure similarity and genetic homology to the SARS-CoV 3CLpro. Quercetin has significant binding affinity to the SARS-CoV-2 S-protein/ACE2 receptor interface. Quercetin also indirectly fights against COVID-19 and related diseases in combination with zinc. In particular, quercetin is a zinc ionophore and may help potentiate zinc's actions on SARS-CoV-2. Additionally, quercetin may produce antiproliferative effects resulting from the modulation of either EGFR or estrogen-receptor mediated signal transduction pathways.

With reference to FIG. 3B, epigallocatechin gallate or EGCG facilitates treatment and prevention of COVID-19 and related diseases by providing both direct and indirect mechanisms of action. In this regard, EGCG directly inhibits 3CLPro and PLpro. EGCG inhibits the 3C-like protease (3CLpro) of SARS-CoV using recombinant 3CLpro expressed in *Pichia pastoris* GS115. As described earlier, SARS-CoV-2 3CLpro has extensive protein structure similarity and genetic homology to the SARS-CoV 3CLpro.

EGCG has also demonstrated strong binding affinity to SARS-CoV-2 PLpro. PLpro is responsible for the cleavages of N-terminus of the replicase poly-protein to release Nsp1, Nsp2 and Nsp3, which is essential for correcting virus replication. PLpro was also confirmed to be significant to antagonize the host's innate immunity. As an indispensable enzyme in the process of coronavirus replication and infection of the host, PLpro has been a popular target for coronavirus inhibitors. It is very valuable for targeting PLpro to treat coronavirus infections, but no inhibitor has been approved by the FDA for marketing.

EGCG also directly inhibits phospholipase A2 (PLA2) which is important for viral entry. Like other coronaviruses, SARS-CoV-2 replication involves extensive membrane rearrangements in infected cells resulting in the formation of double-membrane vesicles (DMVs) and viral replication/transcription complexes (RTCs). Cytosolic phospholipase A2a (cPLA2a) plays an essential role in the production of DMV-associated coronaviral RTCs. EGCG has been shown in vitro to inhibit PLA2 and therefore may indirectly inhibit SARS-CoV-2 replication.

EGCG also indirectly fights against COVID-19 and related diseases in combination with zinc. In particular, EGCG is a zinc ionophore and may help potentiate zinc's actions on SARS-CoV-2.

Caffeic acid is a slightly water-soluble polyphenol with a molar mass of 180.16 g/mol. It is not endogenous in humans and must be obtained through food or supplementation. Based on molecular docking study data, caffeic acid has primary pharmacodynamic effects, including the ability to bind and inhibit SARS-CoV-2 M-protein, E-protein, and N-protein, ultimately affecting SARS-CoV-2 replication and infection. Molecular docking studies have also revealed that caffeic acid may have pharmacological effects allowing it to block SARS-CoV-2 through binding to human host receptor cells. Similarly, and as demonstrated through an in vivo study, caffeic acid has demonstrated ability to inhibit related human coronavirus NL63 (HCoV-NL63) through blocking virus attachment Hesperidin facilitates treatment and prevention of COVID-19 and related diseases by providing several direct mechanisms of action, including the disruption of the spike protein/ACE2 binding, inhibition of helicase, and inhibition of 3CLpro. Hesperidin is an abundant and inexpensive by-product of citrus cultivation and is the major flavonoid in sweet orange and lemon, originally discovered in 1827. No signs of toxicity have been observed with normal intake of hesperidin. Hesperidin has been found to target both the Spike protein as well as the binding interface between Spike and ACE2. Hesperidin has also shown to have a high binding affinity to helicase. Hesperidin has further been found to have high binding affinity to 3CLpro.

Bovine lactoferrin is a water-soluble protein with a molar mass of 3125.8 g/mol and is obtainable through bovine milk. Bovine lactoferrin has provides pharmacodynamic effects that include its ability to inhibit cell-surface heparan sulfate proteoglycans (HSPGs) and ultimately interfere with viral attachment of host cells. Additionally, the pharmaceutical action of bovine lactoferrin has also been studied in other viruses such as Hepatitis C virus.

FIG. 4 provides a table (Table 400) identifying ingredients of one or more additional pharmacological compositions for treating and preventing disease caused by a coronavirus in accordance with one or more additional embodiments of the disclosed subject matter. Repetitive description of like elements employed in respective embodiments is omitted for sake of brevity.

Table 400 identifies five additional active ingredients that can be included in one or more of the disclosed antiviral compositions to further enhance their therapeutic effect. These additional active agents include luteolin, myricetin, pomegranate extract, allicin, ginger, elderberry, and derivatives thereof. In this regard, in some embodiments, one or more of the disclosed antiviral compositions can include one or more of the active ingredients listed in Table 400. The amounts of these additional active agents as included in one or more of the disclosed antiviral compositions can adhere to the following ranges: about 10.0 mg to about 500 mg of luteolin, more preferably about 50.0 mg to about 300 mg of luteolin, and even more preferably about 100 mg to about 200 mg of luteolin; about 50.0 mg to about 800 mg of myricetin, more preferably about 150 mg to about 600 mg of myricetin, and even more preferably about 250 mg of myricetin; about 50.0 mg to about 300 mg of pomegranate extract; about 50.0 mg to about 300 mg of allicin; about 50.0 mg to about 300 mg of ginger; and about 50.0 mg to about 1000 mg of elderberry extract, more preferably between about 150 mg to about 700 mg of elderberry extract, and even more preferably about 300 mg of elderberry extract.

Luteolin also facilitates treatment and prevention of COVID-19 and related diseases by directly binding to the viral S protein, thereby inhibiting the S protein from binding to the human ACE2 receptor interface. Luteolin has demonstrated high binding affinity to the S-protein:ACE2 receptor interface. In addition, Luteolin has also demonstrated high binding affinity to the S2 subunit of SARS-CoV which shares extensive sequence homology with the S protein S2 subunit of SARS-CoV-2.

Myricetin, (also known as cranberry extract) facilitates treatment and prevention of COVID-19 and related diseases by providing several direct mechanisms of action, including inhibition of helicase via myricetin, and viral entry via PAC-A2. Cranberry extract has demonstrated that myricetin (a common flavonoid found in multiple foods, with the highest concentration in cranberry extract) inhibits the SARS-CoV helicase protein by affecting the ATPase activity. SARS-CoV-2 has 99% genetic sequence homology with SARS-CoV helicase. In addition, cranberry extract inhibits viral attachment of COVID-19 to cells and viral entry into cells by mediating the initial interaction with cell receptor. Cranberry extract with high content of A-type proanthocyanidin dimers (PAC-A2) strongly inhibits and exerts virucidal activity against influenza A and B virus replication by preventing attachment and viral entry into target cells through interference with viral hemagglutinin (HA) glycoprotein.

Pomegranate extract, allicin, and ginger enhance adapted and innated immune support of subjects. When n used in combination with one or more other ingredients listed in Tables 100 and 200, these ingredients further facilitate treatment and prevention of COVID-19 and related diseases by providing mechanisms of immune support and correction of micronutrient deficiencies.

Elderberry facilitates treatment and prevention of COVID-19 and related diseases by directly inhibiting viral replication of HCoV-NL63. Elderberry has been shown to have significant antiviral effects in vitro on viral replication of coronavirus HCoV-NL63 which shares sequence homology with SARS-CoV-2. Especially, the elderberry extract of *Sambucus nigra* L. exerts the antiviral activity against influenza A and B viruses, human immunodeficiency virus, and the herpes simplex virus type 1. *Sambucus nigra* phenolic acids like caffeic acid show the highly inhibitory effect on the in vitro replication of influenza A virus.

Also provided are methods of treating and/or preventing disease caused by a coronavirus (and related viruses) in humans and other mammals. The methods typically involve administering one or more of dosages of the disclosed pharmaceutical compositions to the patient daily in an amount sufficient to inhibit growth and/or proliferation of the coronavirus. In various embodiments, the pharmaceutical compounds can be administered orally (e.g., in the form of a capsule, pill, or the like), intravenously or in another suitable form. In certain embodiments the amount is an amount sufficient to exterminate or kill the virus. In some embodiments, the disclosed compositions can be administered to patients who have not contracted COVID-19 (or a related disease) to prevent contracting the disease. In other embodiments, the disclosed compositions can be administered to patients who have tested positive for COVID-19 (or a related disease) to treat the disease to minimize or eliminate the infection (e.g., to kill the virus) and/or to otherwise facilitate recovery from the disease.

Figure 5:
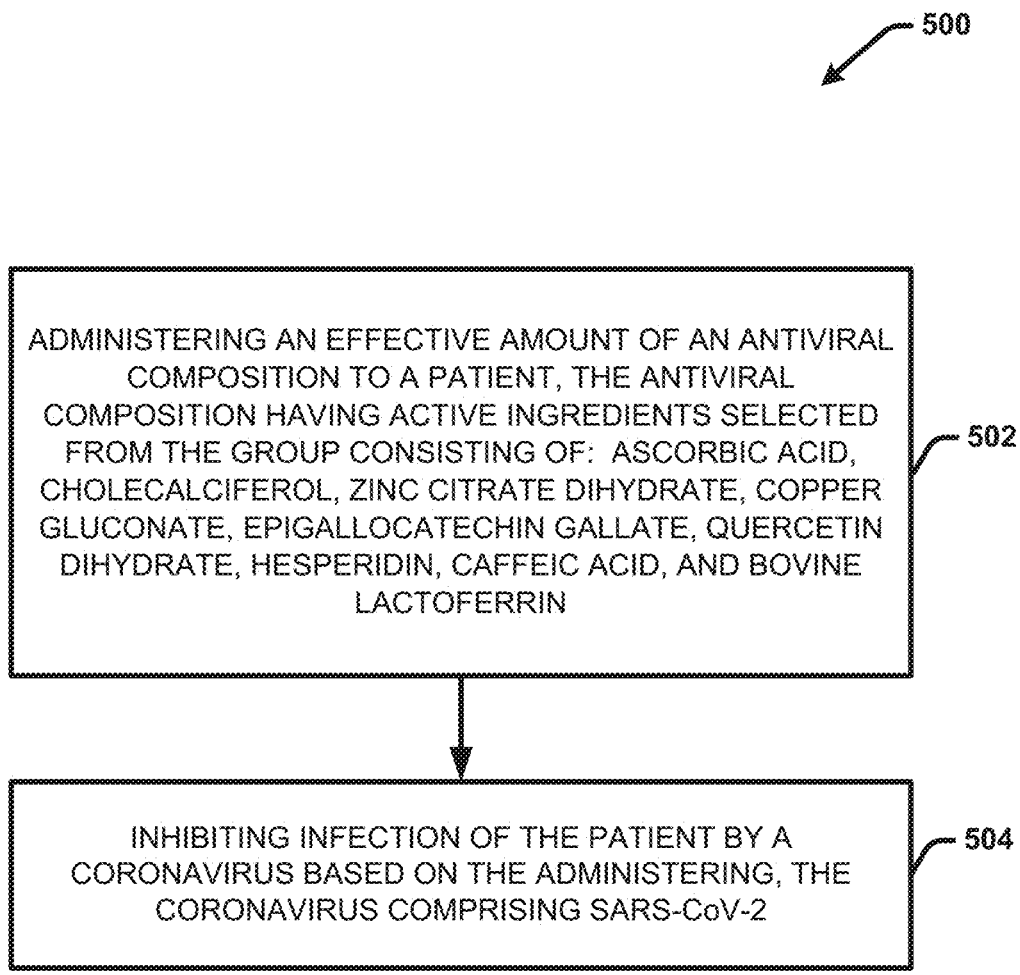
FIG. 5 provides a high-level flow diagram of a method for treating and preventing disease caused by a coronavirus in accordance with one or more embodiments of the disclosed subject matter.

FIG. 5 provides a high-level flow diagram of a method 500 for treating and preventing disease caused by a coronavirus in accordance with one or more embodiments of the disclosed subject matter.

In accordance with method 500, at 502, the method comprises administering an effective amount of an antiviral composition to a patient, the antiviral composition having active ingredients selected from the group consisting of: ascorbic acid, cholecalciferol, zinc (as zinc citrate dihydrate or other forms of elemental zinc), copper (as copper gluconate or other forms of elemental copper), epigallocatechin gallate (or other flavonoids found within green tea), quercetin (as quercetin dihydrate or other forms of quercetin), hesperidin, caffeic acid, bovine lactoferrin, and derivatives of the active ingredients. In some embodiments, the antiviral composition comprises all nine of the above listed active ingredients. In other embodiments, the antiviral composition comprises a subset of the nine listed active ingredients. At 502, the method further comprises inhibiting infection of the patient of by a coronavirus based on the administering, the coronavirus comprising SARS-CoV-2. The effective dose can be tailored based on the patient and the severity of the illness. In some implementations, the antiviral composition can be administered orally in the form of a pill or capsule. For example, each pill or capsule can comprise the relative amounts of the respective active ingredients described above. In some implementations of these embodiments, an effective dose can comprise three capsules taken twice daily for about 10 days.

Figure 6:
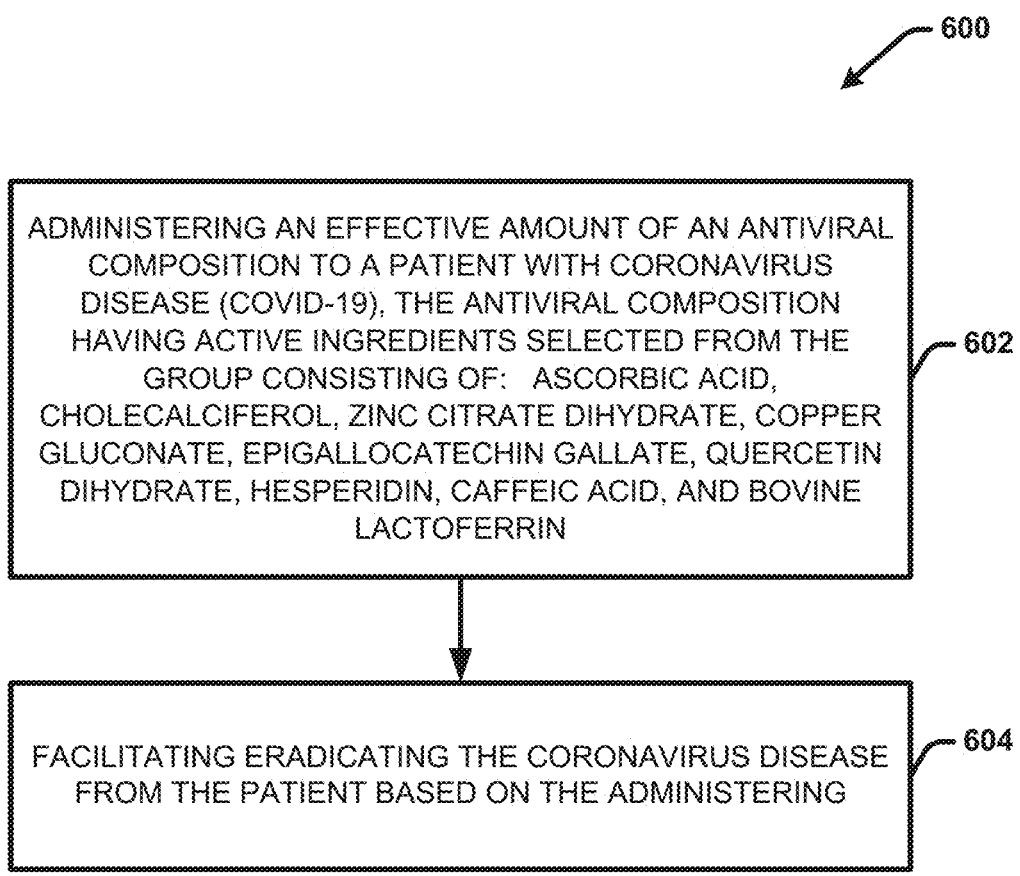
FIG. 6 provides a high-level flow diagram of another method for treating coronavirus disease (COVID-19) in a patient in accordance with one or more embodiments of the disclosed subject matter.

FIG. 6 provides a high-level flow diagram of another method 600 for treating coronavirus disease (COVID-19) in a patient in accordance with one or more embodiments of the disclosed subject matter. Repetitive description of like elements employed in respective embodiments is omitted for sake of brevity.

In accordance with method 600, at 602, the method comprises administering an effective amount of an antiviral composition to a patient with coronavirus disease (COVID-19), the antiviral composition having active ingredients selected from the group consisting of: ascorbic acid, cholecalciferol, zinc (as zinc citrate dihydrate or other forms of elemental zinc), copper (as copper gluconate or other forms of elemental copper), epigallocatechin gallate (or other flavonoids found within green tea), quercetin (as quercetin dihydrate or other forms of quercetin), hesperidin, caffeic acid, bovine lactoferrin, and derivatives of the active ingredients. In some embodiments, the antiviral composition comprises all nine of the above listed active ingredients. In other embodiments, the antiviral composition comprises a subset of the nine listed active ingredients. At 604, method 600 further comprises facilitating eradicating the coronavirus disease from the patient based on the administering. The effective dose can be tailored based on the patient and the severity of the illness. In some implementations, the antiviral composition can be administered orally in the form of a pill or capsule. For example, each pill or capsule can comprise the relative amounts of the respective active ingredients described above. In some implementations of these embodiments, an effective dose can comprise three capsules taken twice daily for about 10 days.

Figure 7:
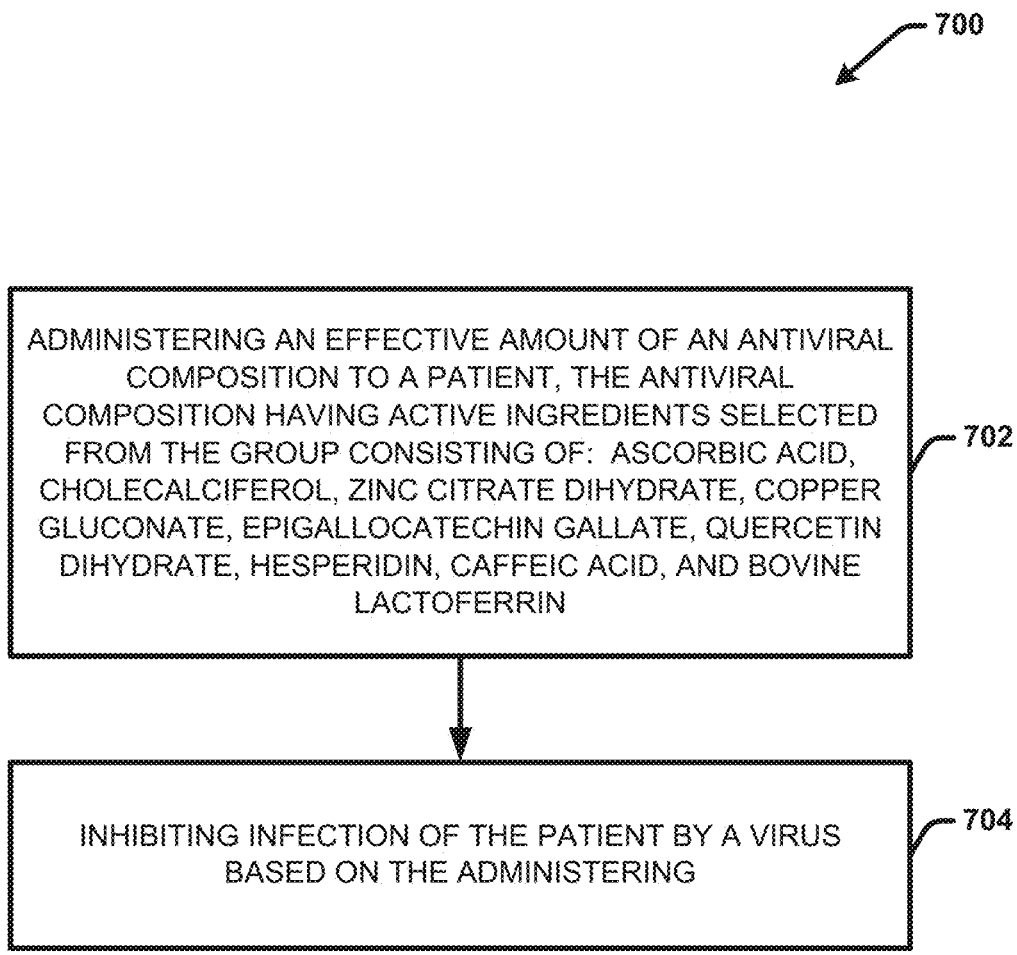
FIG. 7 provides a high-level flow diagram of a method for inhibiting a viral disease in a patient in accordance with one or more embodiments of the disclosed subject matter.

FIG. 7 provides a high-level flow diagram of a method 700 for treating and preventing a viral disease (not limited to COVID-19) in accordance with one or more embodiments of the disclosed subject matter.

In accordance with method 700, at 702, the method comprises administering an effective amount of an antiviral composition to a patient, the antiviral composition having active ingredients selected from the group consisting of: ascorbic acid, cholecalciferol, zinc (as zinc citrate dihydrate or other forms of elemental zinc), copper (as copper gluconate or other forms of elemental copper), epigallocatechin gallate (or other flavonoids found within green tea), quercetin (as quercetin dihydrate or other forms of quercetin), hesperidin, caffeic acid, bovine lactoferrin and derivatives of the active ingredients. In some embodiments, the antiviral composition comprises all nine of the above listed active ingredients. In other embodiments, the antiviral composition comprises a subset of the nine listed active ingredients. At 702, the method further comprises inhibiting infection of the patient of by a virus based on the administering. The effective dose can be tailored based on the patient and the severity of the illness. In some implementations, the antiviral composition can be administered orally in the form of a pill or capsule. For example, each pill or capsule can comprise the relative amounts of the respective active ingredients described above. In some implementations of these embodiments, an effective dose can comprise three capsules taken twice daily for about 10 days.

Figure 8:
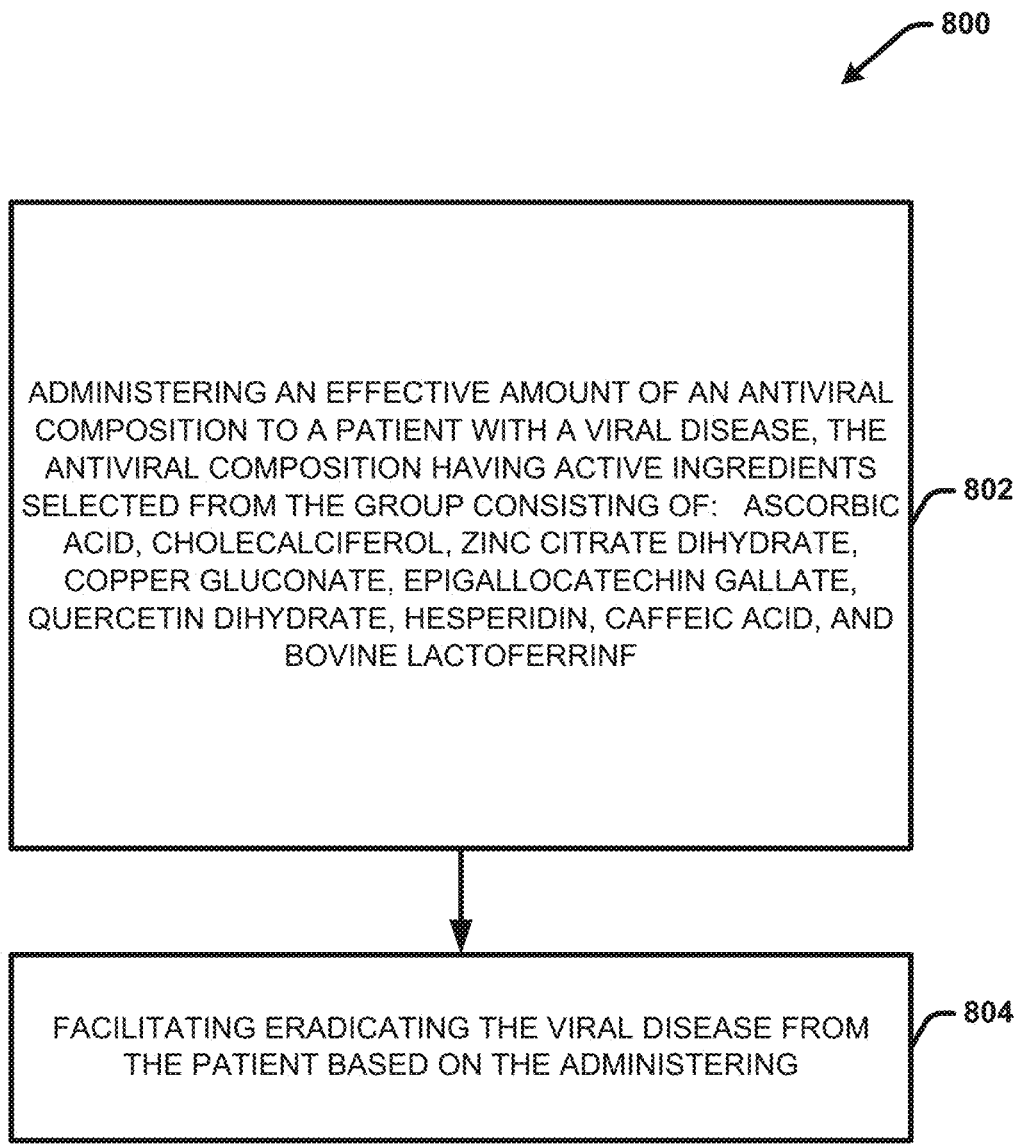
FIG. 8 provides a high-level flow diagram of another method for treating a viral disease in a patient in accordance with one or more embodiments of the disclosed subject matter.

FIG. 8 provides a high-level flow diagram of another method 800 for treating a viral disease (not limited to COVID-19) in a patient in accordance with one or more embodiments of the disclosed subject matter. Repetitive description of like elements employed in respective embodiments is omitted for sake of brevity.

In accordance with method 700, at 702, the method comprises administering an effective amount of an antiviral composition to a patient with a viral disease, the antiviral composition having active ingredients selected from the group consisting of: ascorbic acid, cholecalciferol, zinc (as zinc citrate dihydrate or other forms of elemental zinc), copper (as copper gluconate or other forms of elemental copper), epigallocatechin gallate (or other flavonoids found within green tea), quercetin (as quercetin dihydrate or other forms of quercetin), hesperidin, caffeic acid, bovine lactoferrin and derivatives of the active ingredients. In some embodiments, the antiviral composition comprises all nine of the above listed active ingredients. In other embodiments, the antiviral composition comprises a subset of the nine listed active ingredients. At 804, method 800 further comprises facilitating eradicating the viral disease from the patient based on the administering. The effective dose can be tailored based on the patient and the severity of the viral disease. In some implementations, the antiviral composition can be administered orally in the form of a pill or capsule. For example, each pill or capsule can comprise the relative amounts of the respective active ingredients described above. In some implementations of these embodiments, an effective dose can comprise three capsules taken twice daily for about 10 days.

It should be noted that, for simplicity of explanation, in some circumstances the computer-implemented methodologies are depicted and described herein as a series of acts. It is to be understood and appreciated that the subject innovation is not limited by the acts illustrated and/or by the order of acts, for example acts can occur in various orders and/or concurrently, and with other acts not presented and described herein.

The term "facilitate" as used herein is in the context of a system, device or component "facilitating" one or more actions or operations, in respect of the nature of complex computing environments in which multiple components and/or multiple devices can be involved in some computing operations. Non-limiting examples of actions that may or may not involve multiple components and/or multiple devices comprise transmitting or receiving data, establishing a connection between devices, determining intermediate results toward obtaining a result (e.g., including employing ML and/or AI techniques to determine the intermediate results), etc. In this regard, a computing device or component can facilitate an operation by playing any part in accomplishing the operation. When operations of a component are described herein, it is thus to be understood that where the operations are described as facilitated by the component, the operations can be optionally completed with the cooperation of one or more other computing devices or components, such as, but not limited to: sensors, antennae, audio and/or visual output devices, other devices, etc.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A composition for the treatment of disease caused by a coronavirus, the composition having active ingredients comprising: ascorbic acid, cholecalciferol, zinc citrate dihydrate, copper gluconate, epigallocatechin gallate, quercetin dihydrate, hesperidin, caffeic acid, and bovine lactoferrin, wherein the composition is discretized into units, and wherein each unit comprises about 30.0 milligrams (mg) to about 120 mg of the ascorbic acid, about 5.0 micrograms (μg) to about 50.0 μg of the cholecalciferol, about 0.5 mg to about 20 mg of the zinc citrate dihydrate, about 0.05 mg to about 5.0 mg of the copper gluconate, about 10.0 mg to about 100 mg of the epigallocatechin gallate, about 50.0 mg to about 150 mg of the quercetin dihydrate, about 30.0 mg to about 120 mg of the hesperidin, about 10.0 mg to about 100 mg of the caffeic acid, and about 10.0 mg to about 100 mg of the bovine lactoferrin, and wherein the coronavirus is selected from the group consisting of: severe acute respiratory syndrome (SARS) coronavirus and derivatives thereof, and severe acute respiratory syndrome coronavirus 2 (SARS-COV-2) and derivatives thereof.

2. The composition of claim 1, wherein the active ingredients further comprise derivatives of the active ingredients.

3. The composition of claim 1, wherein the active ingredients further comprise one or more ingredients selected from the group consisting of: luteolin, myricetin, pomegranate extract, allicin, ginger, elderberry, and derivatives thereof.

4. The composition of claim 1, wherein the coronavirus comprises coronavirus disease 19 (COVID-19) in humans and other mammals.

5. The composition of claim 1, wherein the composition further comprises at least one of a pharmaceutically acceptable additive, excipient, or filler.

6. The composition of claim 1, wherein the composition is in a unit form selected from the group consisting of: an oral capsule, a tablet, a liquid and a powder.

7. The composition of claim 1, wherein the composition treats and inhibits infection of the coronavirus in human cells using different mechanisms of action attributed to one or more synergistic combinations of the active ingredients.

8. The composition of claim 1, wherein the composition treats and inhibits infection of the coronavirus in human cells based on direct or indirect disruption of one or more biological targets of the coronavirus caused by one or more of the active ingredients.

9. The composition of claim 8, wherein the one or more biological targets are selected from a group consisting of: spike protein, helicase (nsp13), RNA-dependent RNA polymerase (RdRp), propapain-like protease (PLpro), and chymotrypsin-like protease (3CLpro).

* * * * *